(12) United States Patent
Abe et al.

(10) Patent No.: US 12,209,982 B2
(45) Date of Patent: Jan. 28, 2025

(54) GAS DETECTION SYSTEM FOR DETECTING A TYPE AND CONCENTRATION OF A GAS IN A SAMPLE GAS

(71) Applicant: KYOCERA Corporation, Kyoto (JP)

(72) Inventors: Shinichi Abe, Uji (JP); Daisuke Ueyama, Nara (JP); Etsuro Shimizu, Uji (JP)

(73) Assignee: KYOCERA CORPORATION, Kyoto (JP)

( * ) Notice: Subject to any disclaimer, the term of this patent is extended or adjusted under 35 U.S.C. 154(b) by 505 days.

(21) Appl. No.: 17/440,011

(22) PCT Filed: Mar. 19, 2020

(86) PCT No.: PCT/JP2020/012514
§ 371 (c)(1),
(2) Date: Sep. 16, 2021

(87) PCT Pub. No.: WO2020/189785
PCT Pub. Date: Sep. 24, 2020

(65) Prior Publication Data
US 2022/0170873 A1   Jun. 2, 2022

(30) Foreign Application Priority Data
Mar. 20, 2019   (JP) ................... 2019-053322

(51) Int. Cl.
*G01N 27/12*   (2006.01)
*G01N 33/00*   (2006.01)

(52) U.S. Cl.
CPC ....... *G01N 27/122* (2013.01); *G01N 33/0004* (2013.01)

(58) Field of Classification Search
CPC ............. G01N 33/0004; G01N 1/2273; G01N 1/2247; G01N 33/0006; G01N 33/007; G01N 33/0026; G01N 33/0009
See application file for complete search history.

(56) References Cited

U.S. PATENT DOCUMENTS 6,128,945 A * 10/2000  Shioiri ................. G01N 27/122
                                                              73/31.06
7,216,527 B2 * 5/2007  Imoto ................ G01N 33/0009
                                                              73/1.06

(Continued)

FOREIGN PATENT DOCUMENTS

JP     2000-292403 A      10/2000
JP     2000292402 A    *  10/2000
(Continued)

*Primary Examiner* — Tran M. Tran
(74) *Attorney, Agent, or Firm* — Procopio, Cory, Hargreaves & Savitch LLP

(57) ABSTRACT

A gas detection system includes a sensor unit that outputs a voltage corresponding to a concentration of a specific gas, a supply unit, and a control unit. The supply unit is capable of supplying a sample gas and a purge gas to the sensor unit. The control unit controls the supply unit to alternately supply the sample gas and the purge gas to the sensor unit. The control unit acquires a voltage waveform output by the sensor unit and detects a type and concentration of a gas contained in the sample gas, using a multiple regression analysis using characteristics of the voltage waveform as explanatory variables.

12 Claims, 17 Drawing Sheets

(56) References Cited

U.S. PATENT DOCUMENTS

| | | | | |
|---|---|---|---|---|
| 7,671,600 | B2* | 3/2010 | Suzuki | G01N 27/407 |
| | | | | 324/465 |
| 7,805,974 | B2* | 10/2010 | Scheffler | G01N 33/007 |
| | | | | 73/1.06 |
| 8,166,800 | B2* | 5/2012 | Ieda | G01N 27/407 |
| | | | | 73/31.05 |
| 8,317,998 | B2* | 11/2012 | Pratt | G01N 27/404 |
| | | | | 73/1.06 |
| 9,201,035 | B2* | 12/2015 | Chuang | G01N 27/12 |
| 9,228,865 | B2* | 1/2016 | Andraos | G01D 18/00 |
| 9,417,207 | B2* | 8/2016 | Marra | G01N 27/403 |
| 9,885,695 | B2* | 2/2018 | Nakatani | G01N 21/15 |
| 10,203,302 | B2* | 2/2019 | Buchholz | G01N 27/4163 |
| 10,393,763 | B2* | 8/2019 | Kita | G01N 1/22 |
| 10,466,221 | B2* | 11/2019 | Yocum | G01N 33/004 |
| 10,627,382 | B2* | 4/2020 | Knoefler | F01N 11/00 |
| 11,079,363 | B2* | 8/2021 | Dinsmore | G01N 27/404 |
| 11,326,988 | B2* | 5/2022 | Abe | G01N 27/12 |
| 11,447,387 | B2* | 9/2022 | Jost | B67D 7/342 |
| 11,703,484 | B2 | 7/2023 | Abe | |
| 2003/0054576 | A1* | 3/2003 | Ryu | H01L 22/26 |
| | | | | 257/E21.528 |
| 2010/0262034 | A1* | 10/2010 | Kawata | G01N 30/6095 |
| | | | | 73/23.39 |
| 2014/0290334 | A1* | 10/2014 | Friedrich | G01N 33/0047 |
| | | | | 73/23.2 |
| 2018/0299404 | A1* | 10/2018 | Nunome | G01N 27/4163 |
| 2022/0170873 | A1 | 6/2022 | Abe et al. | |
| 2023/0063005 | A1* | 3/2023 | Nakao | G01N 33/007 |

FOREIGN PATENT DOCUMENTS

| | | |
|---|---|---|
| JP | 2016-142584 A | 8/2016 |
| WO | 2019/022081 A1 | 1/2019 |
| WO | 2020/189785 A1 | 9/2020 |

* cited by examiner

GAS DETECTION SYSTEM FOR DETECTING A TYPE AND CONCENTRATION OF A GAS IN A SAMPLE GAS

CROSS REFERENCE TO RELATED APPLICATIONS

The present application claims priority to Japanese Patent Application No. 2019-053322 filed in Japan on Mar. 20, 2019, the entire disclosure of which is incorporated herein by reference.

TECHNICAL FIELD

The present disclosure relates to a gas detection system.

BACKGROUND ART

In the related art, there is known a system for detecting an odoriferous gas generated from feces discharged by a subject (for example, PTL 1).

CITATION LIST

Patent Literature

PTL 1: Japanese Unexamined Patent Application Publication No. 2016-142584

SUMMARY OF INVENTION

A gas detection system according to an embodiment of the present disclosure includes:
a sensor unit that outputs a voltage corresponding to a concentration of a specific gas;
a supply unit capable of supplying a sample gas and a purge gas to the sensor unit; and
a control unit that controls the supply unit to alternately supply the sample gas and the purge gas to the sensor unit, wherein
the control unit
acquires a voltage waveform output by the sensor unit, and detects a type and concentration of a gas contained in the sample gas, using a multiple regression analysis that uses characteristics of the voltage waveform as explanatory variables.

DESCRIPTION OF EMBODIMENTS

Conventional systems are susceptible to improvement. The present disclosure relates to providing an improved gas detection system.

According to an embodiment of the present disclosure, an improved gas detection system can be provided.

An embodiment according to the present disclosure will be described hereinafter with reference to the drawings. The drawings are schematic illustrations.

Example Configuration of Gas Detection System

Figure 1:
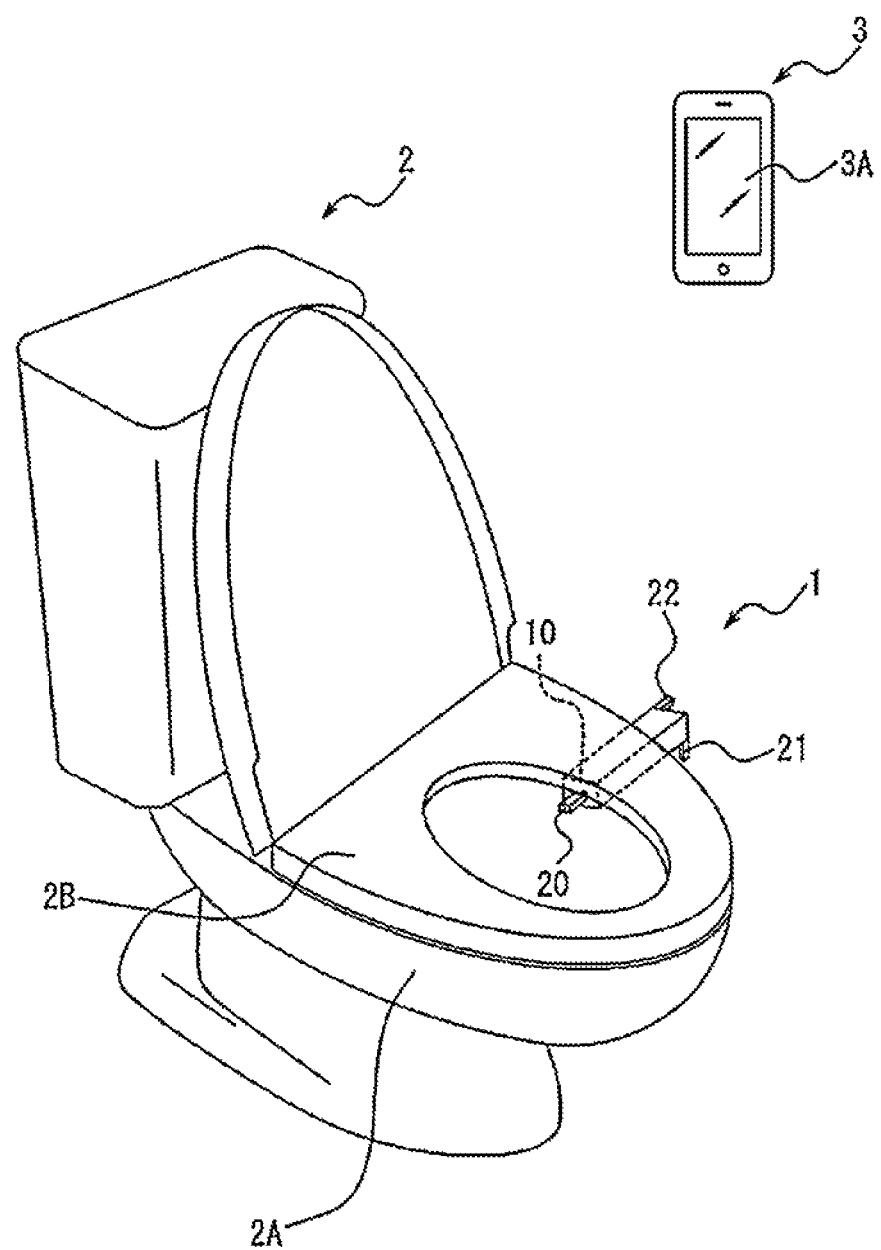
FIG. 1 is an external view of a gas detection system according to an embodiment of the present disclosure.

A gas detection system 1 as illustrated in FIG. 1 is also referred to as a "gas detection device". As illustrated in FIG. 1, the gas detection system 1 is installed in a toilet 2. For example, the toilet 2 may be a flush toilet. The gas detection system 1 may be installed in any portion of the toilet 2. In one example, as illustrated in FIG. 1, the gas detection system 1 may be arranged from between a toilet bowl 2A and a toilet seat 2B to the outside of the toilet 2. A portion of the gas detection system 1 may be embedded inside the toilet seat 2B. A subject can discharge feces into the toilet bowl 2A of the toilet 2. The gas detection system 1 can acquire a gas generated from the feces discharged into the toilet bowl 2A as a sample gas. The gas detection system 1 can detect the type of a gas contained in the sample gas, the concentration of the gas, and so on. The gas detection system 1 can transmit the detection results and so on to an electronic device 3.

The uses of the gas detection system 1 are not limited to the use described above. For example, the gas detection system 1 may be installed in a refrigerator. In this case, the gas detection system 1 can acquire a gas generated from food as a sample gas. In another use, for example, the gas detection system 1 may be installed in a factory or a laboratory. In this case, the gas detection system 1 can acquire a gas generated from a chemical or the like as a sample gas.

The toilet 2 can be installed in a toilet room in a house, a hospital, or the like. The toilet 2 can be used by the subject.

The toilet 2 includes the toilet bowl 2A and the toilet seat 2B. The subject can discharge feces into the toilet bowl 2A.

The electronic device 3 is, for example, a smartphone used by the subject. However, the electronic device 3 is not limited to the smartphone and may be any electronic device. When brought into the toilet room by the subject, as illustrated in FIG. 1, the electronic device 3 can be present in the toilet room. However, for example, when the subject does not bring the electronic device 3 into the toilet room, the electronic device 3 may be present outside the toilet room. The electronic device 3 can receive the detection results from the gas detection system 1 via wireless communication or wired communication. The electronic device 3 can display the received detection results on a display unit 3A. The display unit 3A may include a display capable of displaying characters, and a touch screen capable of detecting contact of a finger of the user (subject) or the like. The display may include a display device such as a liquid crystal display (LCD), an organic EL display (OELD: Organic Electro-Luminescence Display), or an inorganic EL display YIELD: Inorganic Electro-Luminescence Display). The detection method of the touch screen may be any method such as a capacitance method, a resistance film method, a surface acoustic wave method (or an ultrasonic method), an infrared method, an electromagnetic induction method, or a load detection method.

Figure 2:
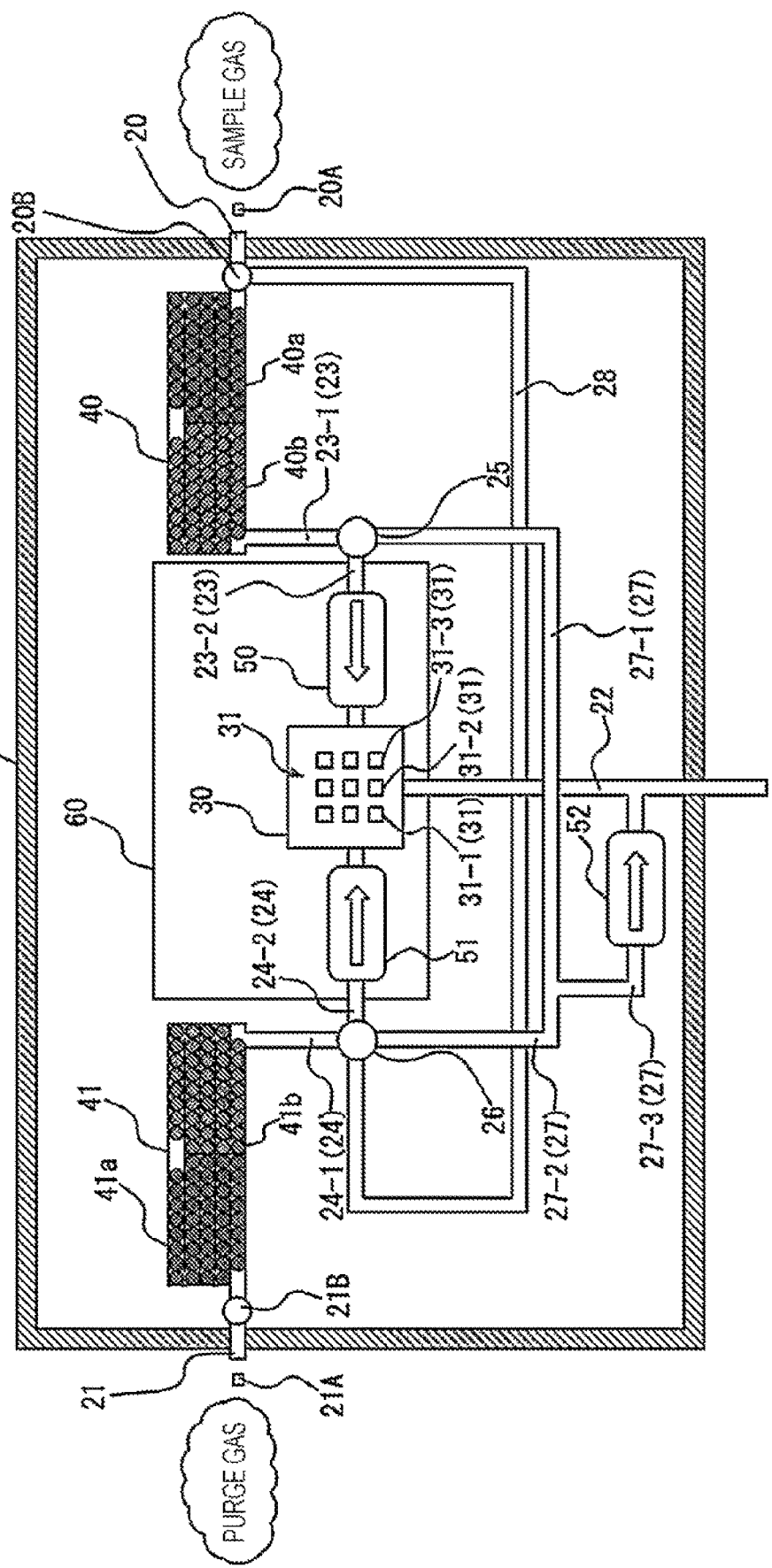
FIG. 2 is a schematic diagram of the inside of a housing of the gas detection system illustrated in FIG. 1.
Figure 3:
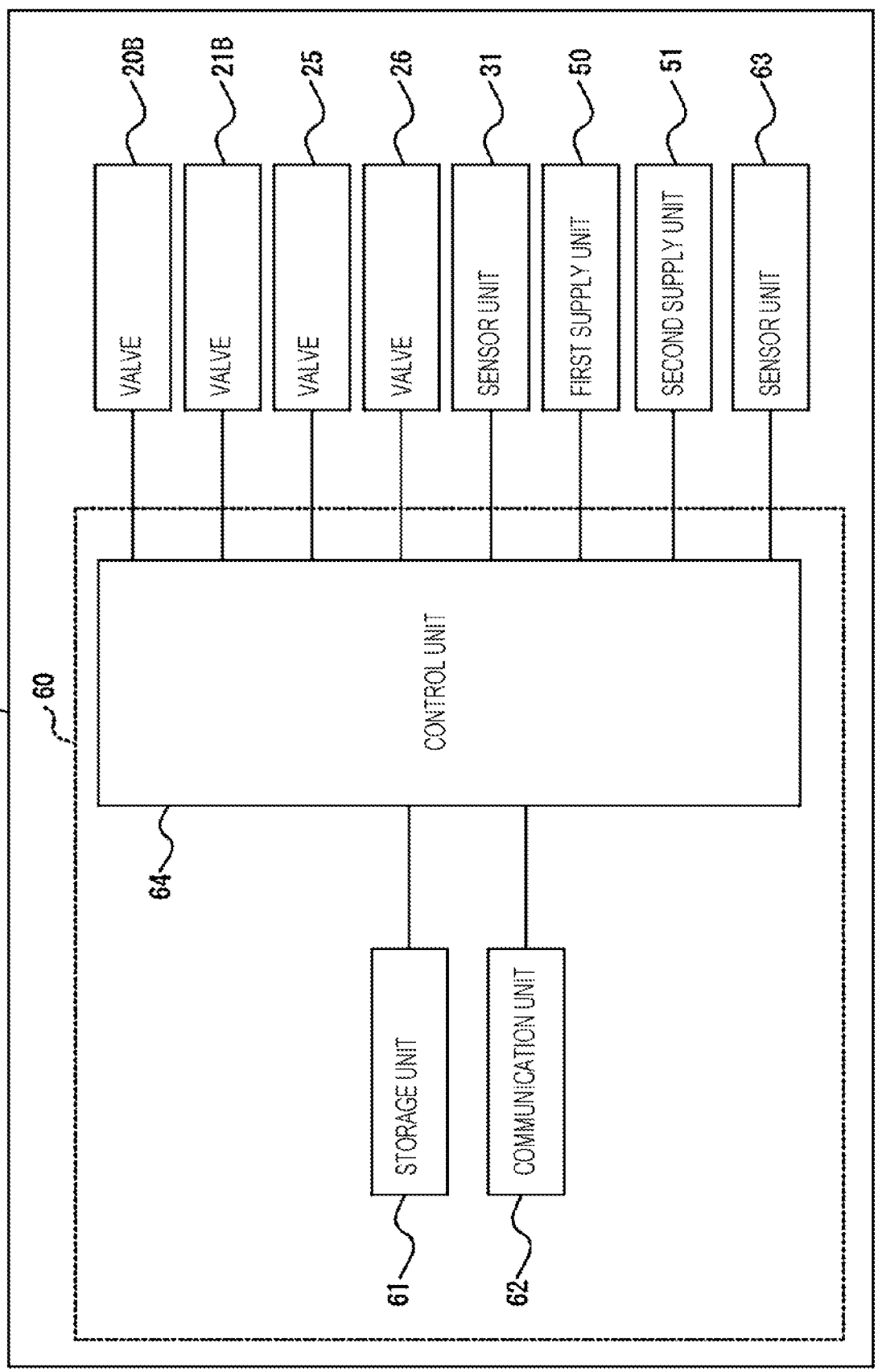
FIG. 3 is a functional block diagram of the gas detection system illustrated in FIG. 1.

As illustrated in FIG. 2, the gas detection system 1 includes a housing 10, a first suction hole 20, a second suction hole 21, a discharge path 22, flow paths 23 and 24, a chamber 30, a first storage tank 40, a second storage tank 41, a first supply unit 50, a second supply unit 51, and a circuit board 60. The flow path 23 includes a flow path 23-1 and a flow path 23-2. The flow path 24 includes a flow path 24-1 and a flow path 24-2. The gas detection system 1 may include a valve 20B and a valve 21B. The gas detection system 1 may include valves 25 and 26, a flow path 27, a flow path 28, and a third supply unit 52. The flow path 27 includes a flow path 27-1, a flow path 27-2, and a flow path 27-3. As illustrated in FIG. 3, the gas detection system 1 includes, in the circuit board 60, a storage unit 61, a communication unit 62, and a control unit 64. The gas detection system 1 may include a sensor unit 63. The gas detection system 1 may further include a battery, a speaker, and the like.

The housing 10 houses various components of the gas detection system 1. The housing 10 may be made of any material. For example, the housing 10 may be made of a material such as metal or resin.

As illustrated in FIG. 1, the first suction hole 20 can be exposed to the inside of the toilet bowl 2A. A portion of the first suction hole 20 may be embedded in the toilet seat 2B. The first suction hole 20 sucks in a gas generated from feces discharged into the toilet bowl 2A as a sample gas. The sample gas sucked in through the first suction hole 20 is supplied to and stored in the first storage tank 40 via the valve 20B as illustrated in FIG. 2. As illustrated in FIG. 1, one end of the first suction hole 20 may be directed to the inside of the toilet bowl 2A. As illustrated in FIG. 2, the other end of the first suction hole 20 may be connected to the first storage tank 40. The first suction hole 20 may be constituted by a tubular member such as a resin tube or a metal or glass pipe.

As illustrated in FIG. 2, the first suction hole 20 may have, outside thereof, an air blower 20A. The air blower 20A may include a fan and a motor. The air blower 20A can drive the motor to rotate the fan under the control of the control unit 64. The air blower 20A can rotate the fan to draw a gas generated from feces into around the first suction hole 20. The air blower 20A draws a gas generated from feces into around the first suction hole 20, the valve 25 connects the flow path 23-1 and the flow path 23-2 to each other, and the first supply unit 50 is driven to allow the first suction hole 20 to suck in the gas generated from the feces in the toilet bowl 2A.

The valve 20B is located between the first suction hole 20, the first storage tank 40, and the flow path 28. The valve 20B includes a connection port connected to the first suction hole 20, a connection port connected to an inlet portion of the first storage tank 40, and a connection port connected to the flow path 28. The valve 20B may be constituted by a valve such as an electromagnetically driven valve, a piezoelectrically driven valve, or a motor-driven valve.

The valve 20B switches the connection state between the first suction hole 20, the first storage tank 40, and the flow path 28 under the control of the control unit 64. For example, the valve 20B switches the connection state between them to a state in which the first suction hole 20 and the first storage tank 40 are connected to each other, a state in which the first storage tank 40 and the flow path 28 are connected to each other, or a state in which the first suction hole 20, the first storage tank 40, and the flow path 28 are not connected to each other.

When the first suction hole 20 sucks in the sample gas, the valve 20B connects the first suction hole 20 and the first storage tank 40 to each other under the control of the control unit 64. When the sample gas is stored in the first storage tank 40, the valve 20B does not connect the first suction hole 20, the first storage tank 40, and the flow path 28 to each other under the control of the control unit 64. The valve 20B does not connect the first storage tank 40 and the first suction hole 20 to each other, which can reduce the probability that the sample gas in the first storage tank 40 comes into contact with the outside air.

As illustrated in FIG. 1, the second suction hole 21 can be exposed to the outside of the toilet bowl 2A. A portion of the second suction hole 21 may be embedded in the toilet seat 2B. The second suction hole 21 sucks in, for example, air (surrounding gas) in the toilet room outside the toilet bowl 2A as a purge gas. The purge gas sucked in through the second suction hole 21 is supplied to and stored in the second storage tank 41 via the valve 21B as illustrated in FIG. 2. As illustrated in FIG. 1, one end of the second suction hole 21 may be directed to the outside of the toilet 2. As illustrated in FIG. 2, the other end of the second suction hole 21 may be connected to the second storage tank 41. The second suction hole 21 may be constituted by a tubular member such as a resin tube or a metal or glass pipe.

As illustrated in FIG. 2, the second suction hole 21 may have, outside thereof, an air blower 21A. The air blower 21A may include a fan and a motor. The air blower 21A can drive the motor to rotate the fan under the control of the control unit 64. The air blower 21A can rotate the fan to draw the air in the toilet room into around the second suction hole 21. The air blower 21A draws the air in the toilet room into around the second suction hole 21, the valve 26 connects the flow path 24-1 and the flow path 24-2 to each other, and the second supply unit 51 is driven to allow the second suction hole 21 to suck in the air in the toilet room as a purge gas.

The valve 21B is located between the second suction hole 21 and the second storage tank 41. The valve 21B includes a connection port connected to the second suction hole 21, and a connection port connected to an inlet portion of the second storage tank 41. The valve 21B may be constituted by a valve such as an electromagnetically driven valve, a piezoelectrically driven valve, or a motor-driven valve.

The valve 21B switches the connection state between the second suction hole 21 and the second storage tank 41 under the control of the control unit 64. For example, the valve 21B switches the connection state between them to a state in which the second suction hole 21 and the second storage tank 41 are connected to each other or a state in which the second suction hole 21 and the second storage tank 41 are not connected to each other.

When the second suction hole 21 sucks in the purge gas, the valve 21B connects the second suction hole 21 and the second storage tank 41 to each other under the control of the control unit 64. When the purge gas is stored in the second storage tank 41, the valve 21B does not connect the second suction hole 21 and the second storage tank 41 to each other under the control of the control unit 64. The valve 20B does not connect the first storage tank 40 and the first suction hole 20 to each other, which can reduce the probability that the purge gas in the second storage tank 41 comes into contact with the outside air.

As illustrated in FIG. 1, a portion of the discharge path 22 can be exposed to the outside of the toilet bowl 2A. The discharge path 22 discharges the exhaust from the chamber 30 as illustrated in FIG. 2 to the outside. The exhaust can contain the sample gas and the purge gas, which have been subjected to a detection process. The discharge path 22 can further discharge the residual gas or the like in the first storage tank 40 to the outside via the flow path 23-1, the valve 25, the flow paths 27-1 and 27-3, and the third supply unit 52. Further, the discharge path 22 can discharge the residual gas or the like in the second storage tank 41 to the outside via the flow path 24-1, the valve 26, the flow paths 27-2 and 27-3, and the third supply unit 52. The discharge path 22 may be constituted by a tubular member such as a resin tube or a metal or glass pipe.

When the valve 25 connects the flow path 23-1 and the flow path 23-2 to each other, the flow path 23 as illustrated in FIG. 2 supplies the sample gas stored in the first storage tank 40 to the chamber 30 via the first supply unit 50. One end of the flow path 23-1 is connected to an outlet portion of the first storage tank 40. The other end of the flow path 23-1 is connected to the valve 25. One end of the flow path 23-2 is connected to the valve 25. The other end of the flow path 23-2 is connected to the chamber 30. The flow path 23 may be constituted by a tubular member such as a resin tube or a metal or glass pipe.

When the valve 26 connects the flow path 24-1 and the flow path 24-2 to each other, the flow path 24 as illustrated in FIG. 2 supplies the purge gas stored in the second storage tank 41 to the chamber 30 via the second supply unit 51. One end of the flow path 24-1 is connected to an outlet portion of the second storage tank 41. The other end of the flow path 24-1 is connected to the valve 26. One end of the flow path 24-2 is connected to the valve 26. The other end of the flow path 24-2 is connected to the chamber 30. The flow path 24 may be constituted by a tubular member such as a resin tube or a metal or glass pipe.

The valve 25 as illustrated in FIG. 2 is located between the flow path 23-1, the flow path 23-2, and the flow path 27-1. The valve 25 includes a connection port connected to the flow path 23-1, a connection port connected to the flow path 23-2, and a connection port connected to the flow path 27-1. The valve 25 may be constituted by a valve such as an electromagnetically driven valve, a piezoelectrically driven valve, or a motor-driven valve.

The valve 25 switches the connection state between the flow path 23-1, the flow path 23-2, and the flow path 27-1 under the control of the control unit 64. For example, the valve 25 switches the connection state between them to a state in which the flow path 23-1 and the flow path 23-2 are connected to each other or a state in which the flow path 23-1 and the flow path 27-1 are connected to each other.

The valve 26 as illustrated in FIG. 2 is located between the flow path 24-1, the flow path 24-2, and the flow path 27-2. The valve 26 includes a connection port connected to the flow path 24-1, a connection port connected to the flow path 24-2, and a connection port connected to the flow path 27-2. The valve 26 may be constituted by a valve such as an electromagnetically driven valve, a piezoelectrically driven valve, or a motor-driven valve.

The valve 26 switches the connection state between the flow path 24-1, the flow path 24-2, the flow path 27-2, and the flow path 28 under the control of the control unit 64. For example, the valve 26 switches the connection state between them to a state in which the flow path 24-1 and the flow path 24-2 are connected to each other, a state in which the flow path 24-1 and the flow path 27-2 are connected to each other, or a state in which the flow path 24-1 and the flow path 28 are connected to each other.

When the valve 25 connects the flow path 23-1 and the flow path 27-1 to each other, the flow path 27 as illustrated in FIG. 2 supplies the residual gas or the like in the first storage tank 40 to the discharge path 22 via the third supply unit 52. When the valve 26 connects the flow path 24-1 and the flow path 27-2 to each other, the flow path 27 supplies the residual gas or the like in the second storage tank 41 to the discharge path 22 via the third supply unit 52. One end of the flow path 27-1 is connected to the valve 25. The other end of the flow path 27-1 is connected to one end of the flow path 27-3. One end of the flow path 27-2 is connected to the valve 26. The other end of the flow path 27-2 is connected to the one end of the flow path 27-3. The one end of the flow path 27-3 is connected to the other end of the flow path 27-1 and the other end of the flow path 27-2. The other end of the flow path 27-3 is connected to the discharge path 22. The flow path 27 may be constituted by a tubular member such as a resin tube or a metal or glass pipe.

When the valve 26 connects the flow path 24-1 and the flow path 28 to each other and the valve 20B connects the flow path 28 and the first storage tank 40 to each other, the flow path 28 as illustrated in FIG. 2 supplies the purge gas in the second storage tank 41 to the first storage tank 40. Since the purge gas is supplied to the first storage tank 40 via the flow path 28, the sample gas in the first storage tank 40 can be pushed out into the flow path 23-1. One end of the flow path 28 is connected to the valve 20B. The other end of the flow path 28 is connected to the valve 26. The flow path 28 may be constituted by a tubular member such as a resin tube or a metal or glass pipe.

As illustrated in FIG. 2, the chamber 30 has, inside thereof, a sensor unit 31. The chamber 30 may include a plurality of sensor units 31. The plurality of sensor units 31 include sensor units 31-1, 31-2, and 31-3. The chamber 30 may be divided into a plurality of chambers. The sensor units 31 may be disposed in the resulting plurality of chambers 30. The plurality of chambers 30 may be connected to each other. The chamber 30 is connected to the flow path 23-2. The sample gas is supplied to the chamber 30 from the flow path 23-2. The chamber 30 is also connected to the flow path 24-2. The purge gas is supplied to the chamber 30 from the flow path 24-2. The chamber 30 is further connected to the discharge path 22. The chamber 30 discharges the sample gas and the purge gas, which have been subjected to a detection process, from the discharge path 22.

The sensor units 31 are arranged in the chamber 30. The sensor units 31 output voltages corresponding to the concentration of a specific gas to the control unit 64. The specific gas contains a specific gas to be detected and a specific gas not to be detected. When the sample gas is a gas generated from feces, examples of the specific gas to be detected include methane, hydrogen, carbon dioxide, methyl mercaptan, hydrogen sulfide, acetic acid, and trimethylamine. When the sample gas is a gas generated from feces, examples of the specific gas not to be detected include ammonia and water. Each of the plurality of sensor units 31 can output a voltage corresponding to the concentration of at least any one of these gases to the control unit 64. When the purge gas contains the specific gas to be detected described above, the amount of the specific gas can be equal to or smaller than the amount of the specific gas to be detected contained in the sample gas.

Figure 4:
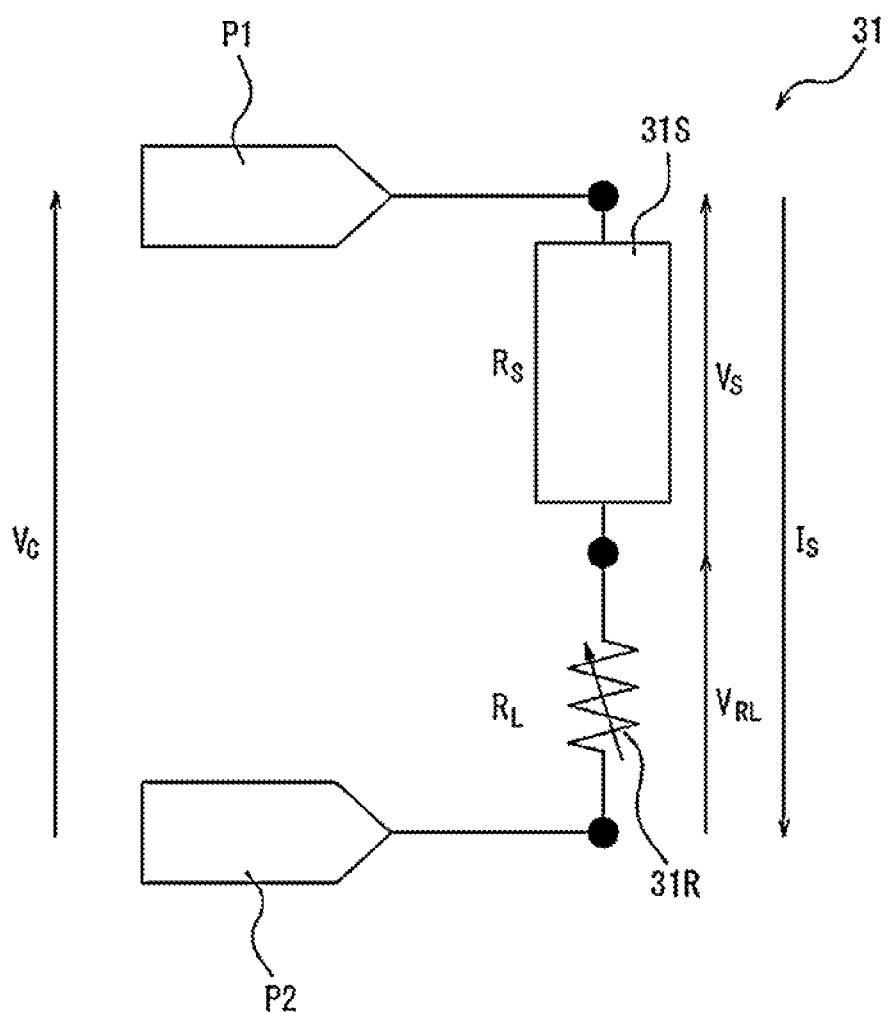
FIG. 4 is a circuit diagram of a sensor unit illustrated in FIG. 2.

As illustrated in FIG. 4, each of the sensor units 31 includes a sensor element 31S and a resistance element 31R. The sensor element 31S and the resistance element 31R are connected in series between a power supply terminal P1 and a ground terminal P2. A voltage value $V_C$ applied between the power supply terminal P1 and the ground terminal P2 can be constant. Since the sensor element 31S and the resistance element 31R are connected in series, the same current value $I_S$ flows to the sensor element 31S and the resistance element 31R. The current value $I_S$ can be determined in accordance with a resistance value $R_S$ of the sensor element 31S and a resistance value $R_{RL}$ of the resistance element 31R. A value that is the sum of a voltage value $V_S$ across the sensor element 31S and a voltage value $V_{RL}$ across the resistance element 31R can be constant (for example, a voltage value $V_C$). The sensor unit 31 may output the voltage value $V_S$ across the sensor element 31S or the voltage value $V_{RL}$ across the resistance element 31R as the voltage corresponding to the concentration of the specific gas.

The power supply terminal P1 as illustrated in FIG. 4 is connected to a power supply such as a battery included in the gas detection system 1. The ground terminal P2 is connected to ground of the gas detection system 1.

As illustrated in FIG. 4, one end of the sensor element 31S is connected to the power supply terminal P1. The other end of the sensor element 31S is connected to one end of the resistance element 31R. The sensor element 31S is a semiconductor sensor. However, the sensor element 31S is not limited to the semiconductor sensor. For example, the sensor element 31S may be a catalytic combustion sensor, a solid electrolyte sensor, or the like.

The sensor element 31S includes a gas-sensitive portion. The gas-sensitive portion includes a metal oxide semiconductor material corresponding to the type of the sensor unit 31. Examples of the metal oxide semiconductor material include a material containing one or more selected from silicon oxides (such as $SnO_2$), indium oxides (such as $In_2O_3$), zinc oxides (such as ZnO), tungsten oxides (such as $WO_3$), iron oxides (such as $Fe_2O_3$), and the like. Adding impurities to the metal oxide semiconductor material of the gas-sensitive portion as appropriate makes it possible to appropriately select a specific gas to be detected by the sensor element 31S. The sensor element 31S may further include a heater for heating the gas-sensitive portion.

When the sensor element 31S is exposed to the purge gas, oxygen contained in the purge gas can be adsorbed on a surface of the gas-sensitive portion of the sensor element 31S. The oxygen adsorbed on the surface of the gas-sensitive portion can capture free electrons on the surface of the gas-sensitive portion. When free electrons are captured by the oxygen adsorbed on the surface of the gas-sensitive portion, the resistance value $R_S$ of the sensor element 31S increases, and the voltage value $V_S$ across the sensor element 31S can increase. That is, when the purge gas is supplied to the sensor unit 31, the voltage value $V_S$ across the sensor element 31S can increase.

When the sensor element 31S is exposed to the sample gas, the specific gas contained in the sample gas is replaced with the oxygen adsorbed on the surface of the gas-sensitive portion of the sensor element 31S, and a reduction reaction can occur. Since the reduction reaction occurs, the oxygen adsorbed on the surface of the gas-sensitive portion can be removed. When the oxygen adsorbed on the surface of the gas-sensitive portion is removed, the resistance value $R_S$ of the sensor element 31S decreases, and the voltage value $V_S$ across the sensor element 31S can decrease. That is, when the sample gas is supplied to the sensor unit 31, the voltage value $V_S$ across the sensor element 31S can decrease in accordance with the concentration of the specific gas contained in the sample gas.

The resistance element 31R is a variable resistance element. The resistance value $R_L$ of the resistance element 31R can be changed in accordance with a control signal from the control unit 64. One end of the resistance element 31R is connected to the other end of the sensor element 31S. The other end of the resistance element 31R is connected to the ground terminal P2.

As described above, when the sample gas is supplied to the sensor unit 31, the voltage value $V_S$ across the sensor element 31S can decrease in accordance with the concentration of the specific gas contained in the sample gas. As described above, furthermore, the value that is the sum of the voltage value $V_S$ across the sensor element 31S and the voltage value $V_{RL}$ across the resistance element 31R is constant. Thus, when the voltage value $V_S$ decreases, the voltage value $V_{RL}$ increases. Therefore, when the sample gas is supplied to the sensor unit 31, the voltage value $V_{RL}$ of the resistance element 31R can increase in accordance with the concentration of the specific gas contained in the sample gas.

As described above, when the purge gas is supplied to the sensor unit 31, the voltage value $V_S$ across the sensor element 31S can increase. As described above, furthermore, the value that is the sum of the voltage value $V_S$ across the sensor element 31S and the voltage value $V_{RL}$ across the resistance element 31R is constant. Thus, when the voltage value $V_S$ increases, the voltage value $V_{RL}$ decreases. Therefore, when the purge gas is supplied to the sensor unit 31, the voltage value $V_{RL}$ of the resistance element 31R can decrease.

Adjusting the resistance value $R_L$ of the resistance element 31R can adjust the voltage value $V_S$ across the sensor element 31S. For example, when the resistance value $R_L$ is set to be equal to the resistance value $R_S$ of the sensor element 31S, the fluctuation range of the voltage value $V_S$ across the sensor element 31S can be close to a maximum value.

As illustrated in FIG. 2, the first storage tank 40 is connected to the first suction hole 20. The first storage tank 40 is capable of storing the sample gas. The sample gas stored in the first storage tank 40 is supplied to the chamber 30 via the flow paths 23-1 and 23-2 and the first supply unit 50. The residual gas or the like in the first storage tank 40 can be discharged to the outside from the discharge path 22 via the flow path 23-1, the valve 25, the flow paths 27-1 and 27-3, and the third supply unit 52.

An adsorbent 40a may be placed in the first storage tank 40. Further, the sample gas may be concentrated in the first storage tank 40. In this case, an adsorbent 40b may be placed in the first storage tank 40. Each of the adsorbent 40a and the adsorbent 40b may contain any material corresponding to the use. Each of the adsorbent 40a and the adsorbent 40b may contain, for example, at least any one of activated carbon, silica gel, zeolite, and molecular sieve. The adsorbent 40a and the adsorbent 40b may be of a plurality of types or may contain a porous material.

The adsorbent 40a may adsorb the gas not to be detected contained in the sample gas. Examples of the adsorbent 40a that adsorbs the gas not to be detected include silica gel and zeolite.

The adsorbent 40b may adsorb the gas to be detected contained in the sample gas. Examples of the adsorbent 40b that adsorbs the gas to be detected include activated carbon and molecular sieve. However, the combination of them may be appropriately changed depending on the polarity of gas molecules to be adsorbed.

In the first storage tank 40, the adsorbent 40a may be divided by a wall or the like. Dividing the adsorbent 40a can lengthen the flow path of the gas in the first storage tank 40. The flow path of the gas in the first storage tank 40 is lengthened, which can lengthen the time during which the gas and the adsorbent 40a are in contact with each other. Likewise, in the first storage tank 40, the adsorbent 40b may be divided by a wall or the like. Dividing the adsorbent 40b can lengthen the time during which the gas and the adsorbent 40b are in contact with each other in the first storage tank 40.

The adsorbent 40a may be provided on the side of the first storage tank 40 where the first storage tank 40 is connected to the first suction hole 20. The adsorbent 40b may be provided on the side of the first storage tank 40 where the first storage tank 40 is connected to the flow path 23-1.

The first storage tank 40 may be formed by a tank or the like having a rectangular parallelepiped shape, a cylindrical shape, a bag shape, or a shape that fits in a gap between various components housed inside the housing 10. The first storage tank 40 may be provided with a heater for heating at least one of an inner wall of the first storage tank 40 and the adsorbent 40a.

The entire first storage tank 40 may be divided by a wall or the like. Dividing the entire first storage tank 40 allows the flow path of the gas to have a small cross-sectional area relative to the volume of the flow path of the gas in the first storage tank 40. The flow path of the gas has a small cross-sectional area relative to the volume of the flow path of the gas, which can reduce the contact area between the gas flowing into the first storage tank 40 from the valve 20B and the sample gas stored in the first storage tank 40 when the sample gas is pushed out into the chamber 30 from the first storage tank 40. The contact area between the gas flowing into the first storage tank 40 from the valve 20B and the sample gas stored in the first storage tank 40 is reduced, which makes it less likely that the gas flowing into the first storage tank 40 from the valve 20B is mixed with the sample gas in the first storage tank 40.

As illustrated in FIG. 2, the second storage tank 41 is connected to the second suction hole 21. The second storage tank 41 is capable of storing the purge gas. The purge gas stored in the second storage tank 41 is supplied to the chamber 30 via the flow paths 24-1 and 24-2 and the second supply unit 51. The residual gas or the like in the second storage tank 41 can be discharged to the outside from the discharge path 22 via the flow path 24-1, the valve 26, the flow paths 27-2 and 27-3, and the third supply unit 52.

An adsorbent 41a and an adsorbent 41b may be placed in the second storage tank 41. Each of the adsorbent 41a and the adsorbent 41a may contain any material corresponding to the use. Each of the adsorbent 41a and the adsorbent 41b may contain, for example, at least any one of activated carbon, silica gel, zeolite, and molecular sieve. The adsorbent 41a and the adsorbent 41b may be of a plurality of types or may contain a porous material.

The adsorbent 41a may adsorb the gas not to be detected that can be contained in the purge gas. Examples of the adsorbent 41a that adsorbs the gas not to be detected include silica gel and zeolite. The adsorbent 41b may adsorb the gas to be detected that can be contained in the purge gas. Examples of the adsorbent 41b that adsorbs the gas to be detected include activated carbon and molecular sieve. However, the combination of them may be appropriately changed depending on the polarity of gas molecules to be adsorbed.

In the second storage tank 41, the adsorbent 41a may be divided by a wall or the like. Dividing the adsorbent 41a can lengthen the flow path of the gas in the second storage tank 41. The flow path of the gas in the second storage tank 41 is lengthened, which can lengthen the time during which the gas and the adsorbent 41a are in contact with each other. Likewise, in the second storage tank 41, the adsorbent 41b may be divided by a wall or the like. Dividing the adsorbent 41b can lengthen the time during which the gas and the adsorbent 41b are in contact with each other in the second storage tank 41.

The adsorbent 41a may be provided on the side of the second storage tank 41 where the second storage tank 41 is connected to the second suction hole 21. The adsorbent 41b may be provided on the side of the second storage tank 41 where the second storage tank 41 is connected to the flow path 24-1.

The second storage tank 41 may be formed by a tank or the like having a rectangular parallelepiped shape, a cylindrical shape, a bag shape, or a shape that fits in a gap between various components housed inside the housing 10. The second storage tank 41 may be provided with a heater for heating at least one of an inner wall of the second storage tank 41, the adsorbent 41a, and the adsorbent 41b.

The entire second storage tank 41 may be divided by a wall or the like. Dividing the entire second storage tank 41 allows the flow path of the gas to have a small cross-sectional area relative to the volume of the flow path of the gas in the second storage tank 41. The flow path of the gas has a small cross-sectional area relative to the volume of the flow path of the gas, which can reduce the contact area between the gas flowing into the second storage tank 41 from the valve 21B and the purge gas stored in the second storage tank 41 when the purge gas is pushed out into the chamber 30 from the second storage tank 41. The contact area between the gas flowing into the second storage tank 41 from the valve 21B and the purge gas stored in the second storage tank 41 is reduced, which makes it less likely that the gas flowing into the second storage tank 41 from the valve 21B is mixed with the purge gas in the second storage tank 41. With this configuration, for example, if a gas near the second suction hole 21 is contaminated, the contaminated gas is less likely to be mixed with the purge gas in the second storage tank 41.

As illustrated in FIG. 2, the first supply unit 50 is attached to the flow path 23-2. The first supply unit 50 is capable of supplying the sample gas stored in the first storage tank 40 to the chamber 30 when the valve 25 connects the flow path 23-1 and the flow path 23-2 to each other. For example, the first supply unit 50 supplies the sample gas stored in the first storage tank 40 to the chamber 30 at a predetermined timing under the control of the control unit 64. The arrow illustrated in the first supply unit 50 indicates the direction in which the first supply unit 50 sends the sample gas. The first supply unit 50 may be constituted by a piezoelectric pump, a motor pump, or the like.

As illustrated in FIG. 2, the second supply unit 51 is attached to the flow path 24-2. The second supply unit 51 is capable of supplying the purge gas stored in the second storage tank 41 to the chamber 30 when the valve 26 connects the flow path 24-1 and the flow path 24-2 to each other. For example, the second supply unit 51 supplies the purge gas stored in the second storage tank 41 to the chamber 30 at a predetermined timing under the control of the control unit 64. The arrow illustrated in the second supply unit 51 indicates the direction in which the second supply unit 51 sends the purge gas. The second supply unit 51 may be constituted by a piezoelectric pump, a motor pump, or the like.

As illustrated in FIG. 2, the third supply unit 52 is attached to the flow path 27-3. The third supply unit 52 is capable of supplying the residual gas or the like in the first storage tank 40 to the discharge path 22 when the valve 25 connects the flow path 23-1 and the flow path 27-1 to each other. Further, the third supply unit 52 is capable of supplying the residual gas or the like in the second storage tank 41 to the discharge path 22 when the valve 26 connects the flow path 24-1 and the flow path 27-2 to each other. The third supply unit 52 supplies the residual gas or the like in at least any one of the first storage tank 40 and the second storage tank 41 to the discharge path 22 under the control of the control unit 64. The arrow illustrated in the third supply unit 52 indicates the direction in which the residual gas or the like is sent to the discharge path 22. The third supply unit 52 may be constituted by a piezoelectric pump, a motor pump, or the like.

The third supply unit 52 is capable of supplying the sample gas from the first suction hole 20 to the first storage tank 40 when the valve 20B connects the first suction hole 20 and the first storage tank 40 to each other and the valve 25 connects the flow path 23-1 and the flow path 27-1 to each other. Further, the third supply unit 52 is capable of supplying the purge gas from the second suction hole 21 to the second storage tank 41 when the valve 21B connects the second suction hole 21 and the second storage tank 41 to each other and the valve 26 connects the flow path 24-1 and the flow path 27-2 to each other.

The circuit board 60 as illustrated in FIG. 3 has mounted therein wiring through which an electrical signal propagates, the storage unit 61, the communication unit 62, the control unit 64, and the like.

The storage unit 61 as illustrated in FIG. 3 is constituted by, for example, a semiconductor memory, a magnetic memory, or the like. The storage unit 61 stores various kinds of information and a program for operating the gas detection system 1. The storage unit 61 may function as a work memory.

The storage unit 61 stores, for example, a multiple regression analysis algorithm. The storage unit 61 stores, for example, a model equation in the multiple regression analysis (for example, model equation (2) described below). The storage unit 61 stores information related to a standard gas described below. The storage unit 61 stores, for example, information related to a prediction equation described below (such as information on prediction equation (1) described below), which is determined or updated by the gas detection system 1 or an external server.

The communication unit 62 as illustrated in FIG. 3 is capable of communicating with the electronic device 3 as illustrated in FIG. 1. The communication unit 62 may be capable of communicating with the external server. The communication method used when the communication unit 62 communicates with the electronic device 3 and the external server may be a short-range wireless communication standard, a wireless communication standard for connecting to a mobile phone network, or a wired communication standard. The short-range wireless communication standard may include, for example, WiFi (registered trademark), Bluetooth (registered trademark), infrared, NFC (Near Field Communication), and the like. The wireless communication standard for connecting to a mobile phone network may include, for example, LTE (Long Term Evolution) or a fourth generation or higher mobile communication system, and the like. Alternatively, the communication method used when the communication unit 62 communicates with the electronic device 3 and the external server may be, for example, a communication standard such as LPWA (Low Power Wide Area) or LPWAN (Low Power Wide Area Network).

The sensor unit 63 as illustrated in FIG. 3 may include at least any one of an image camera, a personal identification switch, an infrared sensor, and a pressure sensor, and the like. The sensor unit 63 outputs a detection result to the control unit 64.

For example, when the sensor unit 63 includes an infrared sensor, the sensor unit 63 detects reflected light from an object irradiated with infrared radiation from the infrared sensor, thereby being able to detect that the subject has entered the toilet room. The sensor unit 63 outputs, as a detection result, a signal indicating that the subject has entered the toilet room to the control unit 64.

For example, when the sensor unit 63 includes a pressure sensor, the sensor unit 63 detects a pressure applied to the toilet seat 2B as illustrated in FIG. 1, thereby being able to detect that the subject has sit on the toilet seat 2B. The sensor unit 63 outputs, as a detection result, a signal indicating that the subject has sit on the toilet seat 2B to the control unit 64.

For example, when the sensor unit 63 includes a pressure sensor, the sensor unit 63 detects a reduction in the pressure applied to the toilet seat 2B as illustrated in FIG. 1, thereby being able to detect that the subject has risen from the toilet seat 2B. The sensor unit 63 outputs, as a detection result, a signal indicating that the subject has risen from the toilet seat 2B to the control unit 64.

For example, when the sensor unit 63 includes an image camera, a personal identification switch, and the like, the sensor unit 63 collects data, such as a face image, the sitting height, and the weight. The sensor unit 63 identifies and detects a person from the collected data. The sensor unit 63 outputs, as a detection result, a signal indicating the identified person to the control unit 64.

For example, when the sensor unit 63 includes a personal identification switch and the like, the sensor unit 63 identifies (detects) a person in response to an operation of the personal identification switch. In this case, personal information may be registered (stored) in the storage unit 61 in advance. The sensor unit 63 outputs, as a detection result, a signal indicating the identified person to the control unit 64.

The control unit 64 as illustrated in FIG. 3 includes one or more processors. The one or more processors may include at least any one of a general-purpose processor that reads a specific program to execute a specific function, and a dedicated processor dedicated to a specific process. The dedicated processor may include an application specific IC (ASIC; Application Specific Integrated Circuit). The one or more processors may include a programmable logic device (PLD; Programmable Logic Device). The PLD may include an FPGA (Field-Programmable Gate Array). The control unit 64 may include at least any one of an SoC (System-on-a-chip) and an SiP (System-in-a-Package) with which the one or more processors cooperate.

<Process for Detecting Type and Concentration of Gas>

The control unit 64 causes the air blower 21A to rotate the fan of the air blower 21A to draw the purge gas into around the second suction hole 21. The control unit 64 causes the valve 26 to connect the flow path 24-1 and the flow path 24-2 to each other and controls the second supply unit 51 so that the purge gas drawn into around the second suction hole 21 is sucked in through the second suction hole 21. The control unit 64 causes the purge gas to be sucked in through the second suction hole 21, thereby storing the purge gas in the second storage tank 41. The control unit 64 may cause the purge gas to be sucked in through the second suction hole 21 after a predetermined time elapses after it is detected that the subject has risen from the toilet seat 2B on the basis of the detection result of the sensor unit 63. Further, the control unit 64 may cause the valve 26 to connect the flow path 24-1 and the flow path 27-2 to each other and control the third supply unit 52 to cause the purge gas to be sucked in through the second suction hole 21.

When causing the purge gas to be sucked in through the second suction hole 21, the control unit 64 may store the purge gas in the second storage tank 41 if the cleanliness of the purge gas is high. The control unit 64 may control the second supply unit 51 to supply the purge gas to the chamber 30. Further, the control unit 64 may determine, based on the detection result of the sensor unit 31, whether the cleanliness of the purge gas is high. If the control unit 64 determines that the degree of cleaning the purge gas is high, the control unit 64 may store the purge gas in the second storage tank 41. In this case, the gas detection system 1 may further include a flow path that directly connects the second suction hole 21 and the chamber 30, and a discharge path that directly discharges the gas supplied to the chamber 30 to the outside. The gas detection system 1 may further include, separately from the sensor unit 31, a dedicated sensor unit that detects the cleanliness of the purge gas. The dedicated sensor unit may be disposed at the tip of the second suction hole 21 as illustrated in FIG. 2 or between the second suction hole 21 and the second storage tank 41. In this case, the gas detection system 1 may further include a discharge path that directly discharges the gas supplied to the dedicated sensor unit to the outside.

The control unit 64 causes the air blower 20A to rotate the fan of the air blower 20A to draw the sample gas into around the first suction hole 20. The control unit 64 causes the valve 25 to connect the flow path 23-1 and the flow path 23-2 to each other and controls the first supply unit 50 so that the sample gas drawn into the first suction hole 20 is sucked in through the first suction hole 20. The control unit 64 causes the sample gas to be sucked in through the first suction hole 20, thereby storing the sample gas in the first storage tank 40. The control unit 64 may cause the sample gas to be sucked in through the first suction hole 20 after a predetermined time elapses after it is detected that the subject has sit on the toilet seat 2B on the basis of the detection result of the sensor unit 63. Further, the control unit 64 may cause the valve 25 to connect the flow path 23-1 and the flow path 27-1 to each other and control the third supply unit 52 to cause the sample gas to be sucked in through the first suction hole 20.

When causing the sample gas to be sucked in through the first suction hole 20, the control unit 64 may determine, based on the detection result of the sensor unit 31, whether the degree of contamination of the sample gas is high. If the control unit 64 determines that the degree of contamination of the sample gas is high, the control unit 64 may store the sample gas in the first storage tank 40 and start measurement. In this case, the gas detection system 1 may further include a flow path that directly connects the first suction hole 20 and the chamber 30, and a discharge path that directly discharges the gas supplied to the chamber 30 to the outside. The gas detection system 1 may further include, separately from the sensor unit 31, a dedicated sensor unit that detects the degree of contamination of the sample gas. The dedicated sensor unit may be disposed, for example, at the tip of the first suction hole 20 as illustrated in FIG. 2 or between the first suction hole 20 and the first storage tank 40. In this case, the gas detection system 1 may further include a discharge path that directly discharges the gas supplied to the dedicated sensor unit to the outside.

The control unit 64 controls the second supply unit 51 and the first supply unit 50 to alternately supply the purge gas and the sample gas to the chamber 30. When supplying the purge gas to the chamber 30, the control unit 64 causes the valve 26 to connect the flow path 24-1 and the flow path 24-2 to each other. When supplying the sample gas to the chamber 30, the control unit 64 causes the valve 25 to connect the flow path 23-1 and the flow path 23-2 to each other. However, the control process of the control unit 64 to supply the purge gas and the sample gas to the chamber 30 is not limited to this. For example, the control unit 64 may cause the valve 20B to connect the first storage tank 40 and the flow path 28 to each other and cause the valve 26 to connect the flow path 24-1 and the flow path 28 to each other to supply the purge gas in the second storage tank 41 to the first storage tank 40 from the valve 20B side. The control unit 64 may supply the purge gas to the first storage tank 40 such that the sample gas in the first storage tank 40 is pushed out into the flow path 23-1 by the purge gas to supply the sample gas in the first storage tank 40 to the chamber 30.

The control unit 64 alternately supplies the purge gas and the sample gas to the chamber 30 to acquire a voltage waveform output by the sensor unit 31 of the chamber 30. The control unit 64 may acquire the voltage value $V_S$ across the sensor element 31S of the sensor unit 31 as illustrated in FIG. 4, and acquire the voltage value $V_{RL}$ across the resistance element 31R. For example, the control unit 64 acquires the voltage value $V_{RL}$ across the resistance element 31R to acquire voltage waveforms as illustrated in FIG. 5.

Figure 5:
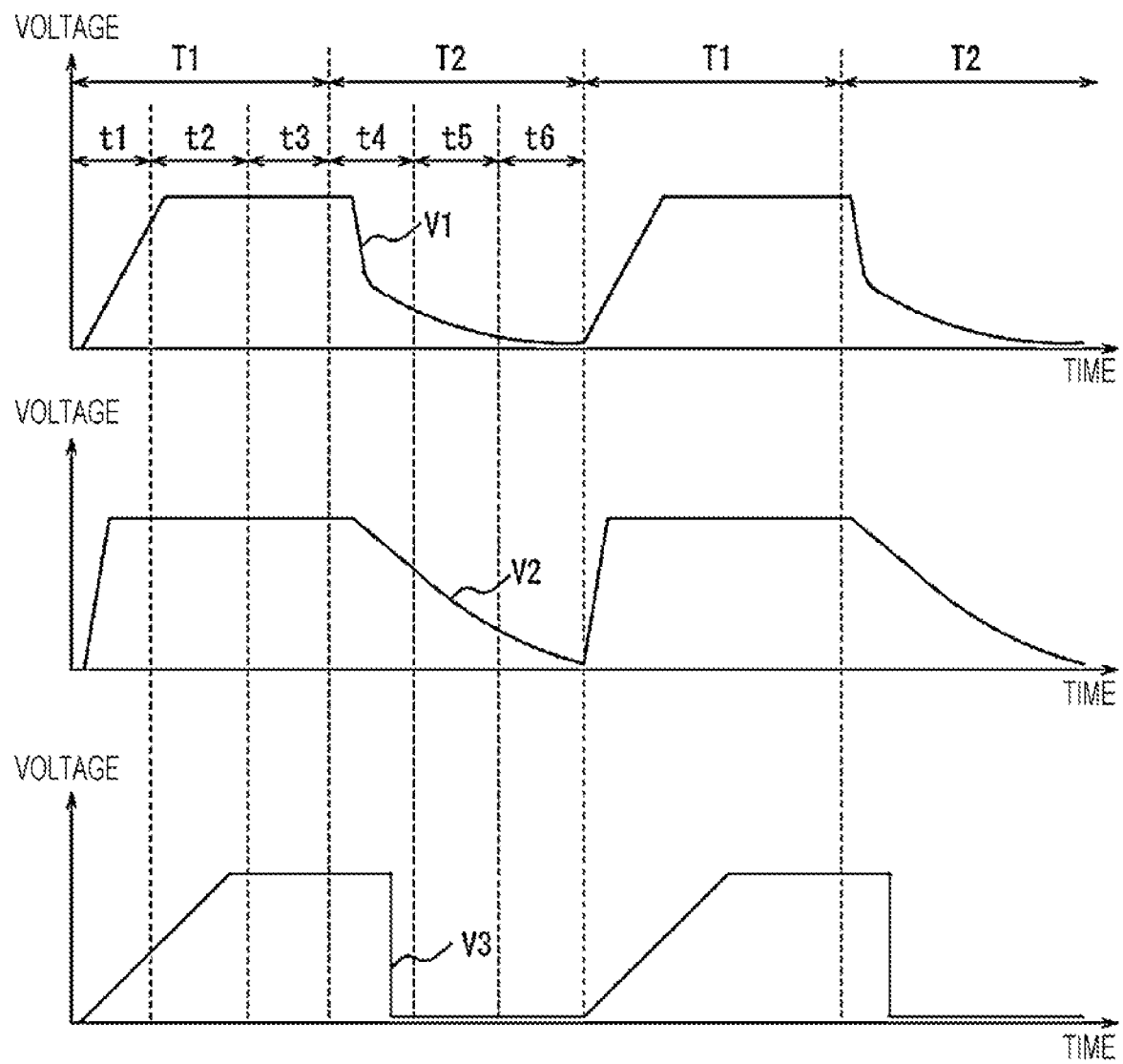
FIG. 5 is a diagram illustrating example voltage waveforms of the sensor unit illustrated in FIG. 2.

FIG. 5 is a diagram illustrating example voltage waveforms of the sensor unit 31 illustrated in FIG. 2. In FIG. 5, the horizontal axis represents time. The vertical axis represents voltage. A voltage value indicated by a voltage waveform V1 is the voltage value $V_{RL}$ across the resistance element 31R of the sensor unit 31-1 as illustrated in FIG. 2. A voltage value indicated by a voltage waveform V2 is the voltage value $V_{RL}$ across the resistance element 31R of the sensor unit 31-2 as illustrated in FIG. 2. A voltage value indicated by a voltage waveform V3 is the voltage value $V_{RL}$ across the resistance element 31R of the sensor unit 31-3 as illustrated in FIG. 2.

In FIG. 5, a first period T1 is a period during which the sample gas stored in the first storage tank 40 is supplied to the chamber 30. As described above, when the sample gas is supplied to the sensor unit 31, the voltage value $V_{RL}$ of the resistance element 31R can increase in accordance with the concentration of the specific gas contained in the sample gas. In the first period T1, accordingly, the voltage values indicated by the voltage waveforms V1 to V3 increase.

In FIG. 5, a second period 12 is a period during which the purge gas stored in the second storage tank 41 is supplied to the chamber 30. As described above, when the purge gas is supplied to the sensor unit 31, the voltage value $V_{RL}$ of the resistance element 31R can decrease. In the second period T2, accordingly, the voltage values indicated by the voltage waveforms V1 to V3 decrease.

The control unit 64 detects the type and concentration of a gas contained in the sample gas, using a multiple regression analysis using as explanatory variables characteristics of the voltage waveform output by the sensor unit 31. The characteristics of the voltage waveform that can be explanatory variables include, for example, a slope, an average value, and a median value of the voltage waveform in a predetermined section, a difference between these numerical values, and the ratio of these numerical values of the sensor unit 31 to those of a different sensor unit 31. In the example illustrated in FIG. 5, sections t1 to t6 can be predetermined sections. The sections t1 to t6 have the same width. However, the sections t1 to t6 may have different widths, as described below. The slope of the voltage waveform in the section t1 can be one of the explanatory variables. The slopes of the voltage waveforms V1 to V3 in the section t1 are represented by "explanatory variable $X_{11}$", "explanatory variable $X_{12}$", and "explanatory variable $X_{13}$", respectively. The slope of the voltage waveform in the section t2 can be one of the explanatory variables. The slopes of the voltage waveforms V1 to V3 in the section t2 are represented by "explanatory variable $X_{21}$", "explanatory variable $X_{22}$", and "explanatory variable $X_{23}$", respectively. The average value of the voltage waveform in the section t3 can be one of the explanatory variables. The average values of the voltage waveforms V1 to V3 in the section t3 are represented by "explanatory variable $X_{31}$", "explanatory variable $X_{32}$", and "explanatory variable $X_{33}$", respectively. The slope of the voltage waveform in the section t4 can be one of the explanatory variables. The slopes of the voltage waveforms V1 to V3 in the section t4 are represented by "explanatory variable $X_{41}$", "explanatory variable $X_{42}$", and "explanatory variable $X_{43}$", respectively. The slope of the voltage waveform in the section t5 can be one of the explanatory variables. The slopes of the voltage waveforms V1 to V3 in the section t5 are represented by "explanatory variable $X_{51}$", "explanatory variable $X_{52}$", and "explanatory variable $X_{53}$", respectively. The average value of the voltage waveform in the section t6 can be one of the explanatory variables. The average values of the voltage waveforms V1 to V3 in the section t6 are represented by "explanatory variable $X_{61}$", "explanatory variable $X_{62}$", and "explanatory variable $X_{63}$", respectively.

The control unit 64 estimates (detects) the type and concentration of the gas contained in the sample gas using a prediction equation determined by the multiple regression analysis and an explanatory variable used in the prediction equation among the explanatory variables. For example, the control unit 64 detects the type and concentration of a gas contained in the sample gas using prediction equation (1) below. Prediction equation (1) is an example of a prediction equation for predicting the concentration of a predetermined gas. Prediction equation (1) is determined by a multiple regression analysis using a mixed gas whose gas composition is known. The process for determining prediction equation (1) will be described below.

$$Y_1 = A \times X_{11} + B \times X_{22} + C \times X_{33} + D \qquad (1)$$

In prediction equation (1), the concentration $Y_1$ is the concentration of a predetermined gas. The coefficients A, B, and C are regression coefficients of the explanatory variables $X_{11}$, $X_{22}$, and $X_{33}$, respectively. The constant D is a constant term. Among the explanatory variables $X_{11}$, $X_{12}$, $X_{13}$, $X_{21}$, $X_{22}$, $X_{23}$, $X_{31}$, $X_{32}$, $X_{33}$, $X_{41}$, $X_{42}$, $X_{43}$, $X_{51}$, $X_{52}$, $X_{53}$, $X_{61}$, $X_{62}$, and $X_{63}$ described above, the explanatory variables $X_{11}$, $X_{22}$, and $X_{33}$ are used in prediction equation (1). In other words, the explanatory variables $X_{12}$, $X_{13}$, $X_{21}$, $X_{23}$, $X_{31}$, $X_{32}$, $X_{41}$, $X_{42}$, $X_{43}$, $X_{51}$, $X_{52}$, $X_{53}$, $X_{61}$, $X_{62}$, and $X_{63}$ are not used in prediction equation (1).

The control unit 64 may acquire information related to the prediction equation from the outside via the storage unit 61 or the communication unit 62. The information related to the prediction equation may include information on the prediction equation, information on an explanatory variable used in the prediction equation, information on a predetermined interval, information on computation for acquiring the explanatory variable, and the like. The predetermined interval is an interval used to divide a voltage waveform into a plurality of sections. The predetermined interval corresponds to the width of the sections t1 to t6 as illustrated in FIG. 5. For example, in the case of prediction equation (1), the information related to the prediction equation can include information on prediction equation (1), information on the explanatory variables $X_{11}$, $X_{22}$, and $X_{33}$ used in prediction equation (1), information on the predetermined interval, and information on computation for acquiring the explanatory variables $X_{11}$, $X_{22}$, and $X_{33}$. For example, upon acquiring the information related to the prediction equation, the control unit 64 divides the voltage waveforms as illustrated in FIG. 5 by the predetermined interval along the time axis into the sections t1 to t6 as a plurality of sections. Further, the control unit 64 calculates, based on the information on computation for acquiring the explanatory variables, the slope of the voltage waveform V1 in the section t1 as illustrated in FIG. 5 to acquire the explanatory variable $X_{11}$. Further, the control unit 64 calculates the average value of the voltage waveform V2 in the section t2 as illustrated in FIG. 5 to acquire the explanatory variable $X_{22}$. Further, the control unit 64 calculates the average value of the voltage waveform V3 in the section t3 as illustrated in FIG. 5 to acquire the explanatory variable $X_{33}$. The control unit 64 substitutes the explanatory variables $X_{11}$, $X_{22}$, and $X_{33}$ into prediction equation (1) described above to estimate (detect) the concentration $Y_1$ of the predetermined gas.

Regarding the widths of the sections corresponding to the explanatory variables, in the example illustrated in FIG. 5, the sections t1 to t6 may not have the same width. For example, the sections corresponding to the explanatory variables may have different widths. The sections corresponding to the explanatory variables may partially overlap. The sections corresponding to the explanatory variables may include a subdivided section for acquiring a certain explanatory variable. The settings of a section corresponding to an appropriate explanatory variable may be appropriately selected in advance according to data of a voltage waveform output by the sensor unit 31, the time interval at which the voltage waveform is acquired, and the magnitude or frequency of noise included in the voltage waveform. Data of all voltage waveforms output by the sensor unit 31 may not be used to detect the type and concentration of the gas. For example, data of only necessary portions of the voltage waveforms output by the sensor unit 31, as appropriate, which is obtained by, for example, removing unnecessary portions, may be used to detect the type and concentration of the gas.

The control unit 64 may use a different prediction equation in accordance with the type of gas. Using a different prediction equation corresponding to the type of gas, the control unit 64 can detect the concentration for each type of gas contained in the sample gas. In other words, the control unit 64 can detect the type and concentration of a gas contained in the sample gas.

The control unit 64 may transmit the detected type and concentration of the gas to the electronic device 3 via the communication unit 62 as a detection result. Further, after the detection process is completed, the control unit 64 may cause the valve 25 to connect the flow path 23-1 and the flow path 27-1 to each other and control the third supply unit 52 to discharge the residual gas in the first storage tank 40 from the discharge path 22. After the detection process is completed, furthermore, the control unit 64 may cause the valve 26 to connect the flow path 24-1 and the flow path 27-2 to each other and control the third supply unit 52 to discharge the residual gas in the second storage tank 41 from the discharge path 22.

<Process for Determining Prediction Equation>

The process for determining a prediction equation below may be executed before shipment, during maintenance, or the like of the gas detection system 1.

The control unit 64 causes the purge gas to be sucked in through the second suction hole 21 in a way similar to that described above in accordance with a program incorporated therein in advance or when a control signal for providing an instruction to suck in the purge gas is received from the outside via the communication unit 62. The control signal for providing an instruction to suck in the purge gas can be transmitted to the gas detection system 1 when a prediction equation is to be determined before shipment or the like of the gas detection system 1. The control unit 64 causes the purge gas to be sucked in through the second suction hole 21 to store the purge gas in the second storage tank 41.

The control unit 64 causes the sample gas to be sucked in through the first suction hole 20 in a way similar to that described above in accordance with a program incorporated therein in advance or when a control signal for providing an instruction to suck in the sample gas is received from the outside via the communication unit 62. The control signal for providing an instruction to suck in the sample gas can be transmitted to the gas detection system 1 when a prediction equation is to be determined before shipment or the like of the gas detection system 1. The control unit 64 causes the sample gas to be sucked in through the first suction hole 20 to store the sample gas in the first storage tank 40. In the process for determining the prediction equation, a mixed gas whose gas composition is known is used as the sample gas. That is, a mixed gas whose gas composition is known is stored in the first storage tank 40. The mixed gas whose gas composition is known is hereinafter referred to also as "standard gas".

The control unit 64 acquires a model equation in the multiple regression analysis from the outside via the storage unit 61 or the communication unit 62. For example, the control unit 64 acquires model equation (2) below.

[Math. 1]

$$Y_n = \Sigma_i \Sigma_j E_{ijn} \times X_{ij} + F \quad (2)$$

In model equation (2), n, i, and j are natural numbers. n corresponds to the type of gas. The gas corresponding to n is hereinafter referred to also as "gas n". i corresponds to a section corresponding to an explanatory variable. The section corresponding to i is hereinafter referred to also as "section i". j corresponds to any one of the plurality of sensor units 31. The sensor unit 31 corresponding to j is hereinafter referred to also as "sensor unit 31*j*". The concentration $Y_n$ is the concentration of the gas n. The explanatory variable $X_{ij}$ is the explanatory variable for the voltage waveform of the sensor unit 31*j* corresponding to the section i. The coefficient $E_{ijn}$ is the coefficient of the explanatory variable $X_{ij}$ for the gas n. The error F is an error term.

The control unit 64 acquires information related to the standard gas from the outside via the storage unit 61 or the communication unit 62. The information related to the standard gas includes information on the type and concentration of a gas contained in the standard gas, and information related to acquisition of an explanatory variable. For example, in the case of model equation (2), the information on the type and concentration of a gas is information on the type and concentration $Y_n$ of the gas n. For example, in the case of model equation (2), the information related to acquisition of an explanatory variable can include information on the section i, and information on computation for acquiring the explanatory variable $X_{ij}$ from the section i of the sensor unit 31*j*.

The control unit 64 alternately supplies the purge gas and the sample gas to the chamber 30 in a way similar to that described above to acquire a voltage waveform output by the sensor unit 31 of the chamber 30. For example, the control unit 64 executes supervised machine learning on the voltage waveform of the sensor unit 31 to acquire an effective explanatory variable and a regression coefficient in model equation (2). The control unit 64 acquires an effective explanatory variable and a regression coefficient to determine a prediction equation of the gas n.

For example, in the case of the concentration $Y_1$ (n=1) of a predetermined gas, the control unit 64 acquires the explanatory variables $X_{11}$, $X_{22}$ and $X_{33}$ as effective explanatory variables. The control unit 64 acquires the coefficient A as the coefficient $E_{111}$ of the explanatory variable $X_{11}$. The control unit 64 acquires the coefficient B as the coefficient $E_{221}$ of the explanatory variable $X_{11}$. The control unit 64 acquires the coefficient C as the coefficient $E_{331}$ of the explanatory variable $X_{33}$. The control unit 64 acquires the constant D as the error F. The control unit 64 acquires the effective explanatory variables $X_{11}$, $X_{22}$, and $X_{33}$, the coefficients A, B, and C, and the constant D to determine prediction equation (1) described above of the concentration $Y_1$ of the predetermined gas. The control unit 64 may store the effective explanatory variables $X_{11}$, $X_{22}$, and $X_{33}$, the coefficients A, B, and C, and the constant D in the storage unit 61.

The control unit 64 can determine a different prediction equation in accordance with the type of gas. Here, the control unit 64 may not learn all of the acquired data of voltage waveforms of the sensor unit 31. The settings of a section corresponding to an appropriate explanatory variable may be appropriately selected in advance according to data of a voltage waveform output by the sensor unit 31, the time interval at which the voltage waveform is acquired, and the magnitude or frequency of noise included in the voltage waveform. Alternatively, a multiple regression analysis including all possible explanatory variables may be used to extract more effective explanatory variables.

<Calibration Process>

The control unit 64 may execute a calibration process for the sensor unit 31 before detecting the type and concentration of a gas.

Specifically, the control unit 64 may acquire the resistance value $R_S$ of the sensor element 31S. The control unit 64 may acquire the resistance value $R_S$ from the voltage value $V_S$ across the sensor element 31S. In this case, the control unit 64 acquires the voltage value $V_S$ across the sensor element 31S. Further, the control unit 64 computes the equation [$R_S=V_S \div I_S$] to acquire the resistance value $R_S$. Alternatively, the control unit 64 may acquire the resistance value $R_S$ from the voltage value $V_{RL}$, across the resistance element 31R. In this case, the control unit 64 acquires the voltage value $V_{RL}$ across the resistance element 31R. Further, the control unit 64 computes the equation [$R_S=(V_C-V_{RL}) \div I_S$] to acquire the resistance value $R_S$.

The control unit 64 determines whether the resistance value $R_S$ of the sensor element 31S falls below a predetermined value. As described above, if a specific gas adheres to the surface of the gas-sensitive portion of the sensor element 31S, the resistance value $R_S$ of the sensor element 31S can decrease. If a specific gas adheres to the surface of the gas-sensitive portion due to a failure or the like of the sensor element 31S, the resistance value $R_S$ of the sensor element 31S may significantly decrease. In this case, it can be difficult for the gas detection system 1 to detect the type and concentration of the gas. To address this, if the control unit 64 determines that the resistance value $R_S$ of the sensor element 31S falls below the predetermined value, the control unit 64 generates a signal indicating an alarm. The predetermined value may be appropriately set in accordance with the material contained in the sensor element 31S. The control unit 64 may transmit the signal indicating an alarm to an external device such as the electronic device 3 via the communication unit 62. When the gas detection system 1 includes a speaker, the control unit 64 may output the signal indicating an alarm to the speaker to cause the speaker to output an alarm sound. In some cases, the resistance value $R_S$ of the sensor element 31S can exceed a second predetermined value larger than the predetermined value due to some abnormality of another sensor. In this case, the control unit 64 may generate an alarm signal similar to that described above or an alarm signal different from the alarm described above. Through the process described above, an abnormality can be sensed.

If the control unit 64 determines that the resistance value $R_S$ of the sensor element 31S is greater than or equal to the predetermined value, the control unit 64 adjusts the resistance value $R_L$ of the resistance element 31R in accordance with the resistance value $R_S$ of the sensor element 31S. For example, the control unit 64 may adjust the resistance value $R_L$ of the resistance element 31R in accordance with the resistance value $R_S$ so that the minimum value of the voltage value $V_{RL}$ in the second period T2 becomes near zero or the maximum value of the voltage value $V_{RL}$ in the first period T1 becomes near $V_C$. The control unit 64 may calculate a maximum value and a minimum value $R_{MIN}$ of the resistance value $R_S$ of the sensor element 31S from the voltage waveform of the sensor unit 31 measured in advance and perform determination using equation (3) described below.

<Resolution Adjustment Process>

The control unit 64 may adjust the resolution of the sensor unit 31. In the present disclosure, the phrase "resolution of a sensor unit" refers to the ability to distinguish the voltage value $V_S$ across the sensor element 31S from noise. Noise is caused by the circuit structure and the like of the gas detection system 1 and can thus be constant. Accordingly, increasing the fluctuation range of the voltage value $V_S$ across the sensor element 31S can increase the ratio of the voltage value $V_S$ to noise. In other words, increasing the fluctuation range of the voltage value $V_S$ across the sensor element 31S can increase the resolution of the sensor unit 31. Here, the fluctuation range of the voltage value $V_S$ can be close to the maximum value if the resistance value $R_L$ of the resistance element 31R as illustrated in FIG. 4 is set to be equal to the resistance value $R_S$ of the sensor element 31S. Accordingly, the control unit 64 sets the resistance value $R_L$ of the resistance element 31R to be equal to the resistance value $R_S$ of the sensor element 31S to increase the resolution of the sensor unit 31. In this case, the control unit 64 acquires the maximum value $R_{MAX}$ of the resistance value $R_S$ of the sensor element 31S and the minimum value $R_{MIN}$ of the resistance value $R_S$ of the sensor element 31S from the voltage waveform output by the sensor unit 31. Further, the control unit 64 calculates the geometric mean value $R_A$ of the maximum value $R_{MAX}$ and the minimum value $R_{MIN}$. For example, the control unit 64 calculates the geometric mean value $R_A$ using equation (3) below. In addition, the control unit 64 outputs a control signal to the resistance element 31R to set the resistance value $R_L$ of the resistance element 31R to the geometric mean value $R_A$.

[Math. 2]

$$R_A = \sqrt{R_{MAX} \times R_{MIN}} \qquad (3)$$

Figure 6:
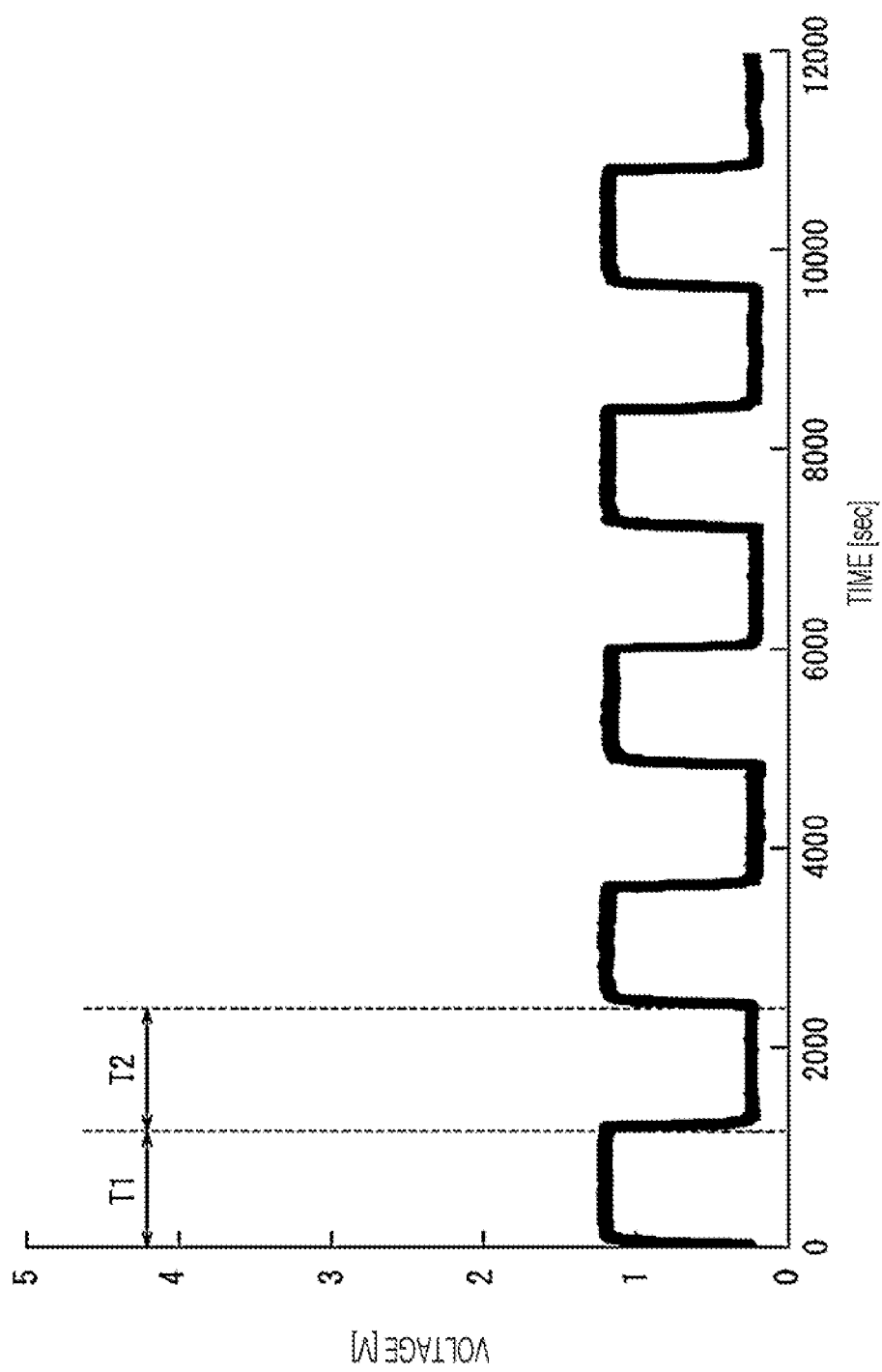
FIG. 6 is a diagram illustrating an example voltage waveform before the adjustment of the resolution of the sensor unit illustrated in FIG. 2.
Figure 7:
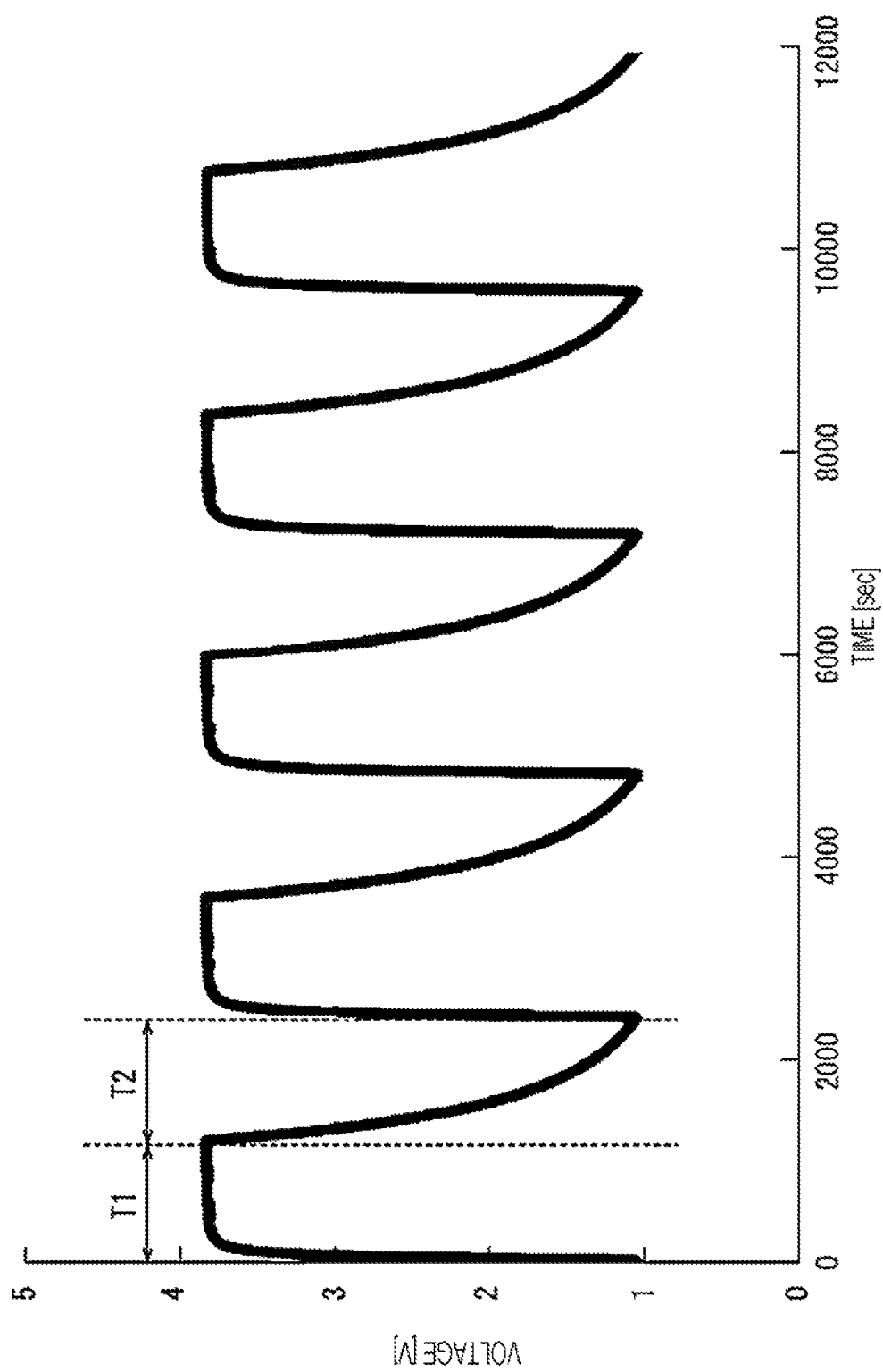
FIG. 7 is a diagram illustrating an example voltage waveform after the adjustment of the resolution of the sensor unit illustrated in FIG. 2.

FIG. 6 is a diagram illustrating an example voltage waveform before the adjustment of the resolution of the sensor unit 31 illustrated in FIG. 2. FIG. 7 is a diagram illustrating an example voltage waveform after the adjustment of the resolution of the sensor unit 31 illustrated in FIG. 2. That is, the voltage waveform as illustrated in FIG. 7 is a voltage waveform obtained after the resistance value $R_L$ of the resistance element 31R is set to the geometric mean value $R_A$. In FIG. 6 and FIG. 7, the horizontal axis represents time. The vertical axis represents voltage.

In FIG. 6 and FIG. 7, the voltage value of the voltage waveform is the voltage value $V_{RL}$ across the sensor element 31S of the sensor unit 31. Thus, as described above, the voltage value $V_{RL}$ increases in the first period T1, and the voltage value $V_{RL}$ decreases in the second period T2. In FIG. 6 and FIG. 7, furthermore, the voltage value $V_C$ applied between the power supply terminal P1 and the ground terminal P2 as illustrated in FIG. 4 is 5 [V].

As illustrated in FIG. 6, before the adjustment of the resolution of the sensor unit 31, the fluctuation range of the voltage value $V_S$ across the sensor element 31S is about 1 [V]. In contrast, as illustrated in FIG. 7, after the adjustment of the resolution of the sensor unit 31, the fluctuation range of the voltage value $V_S$ across the sensor element 31S is about 3.8 [V], and the voltage waveform of the sensor unit 31 crosses over the voltage value Vc/2. That is, the resistance value $R_S$ of the sensor element 31S and the resistance value $R_L$ of the resistance element 31R are equal (resistance value $R_S$=resistance value $R_L$) at the voltage value Vc/2, and the resolution can be maximized. In the voltage waveform as illustrated in FIG. 7, the fluctuation range of the voltage value $V_S$ is larger, and thus the voltage waveform as illustrated in FIG. 7 can be less susceptible to noise than the voltage waveform as illustrated in FIG. 6. In FIG. 7, since the fluctuation range of the voltage value $V_S$ is larger, it is possible to more accurately acquire explanatory variables, which are characteristics of the voltage waveform.

Here, the control unit 64 may acquire the maximum value $R_{MAX}$ and the minimum value $R_{MIN}$ of the resistance value $R_S$ of the sensor element 31S from the section corresponding to the explanatory variable used in the prediction equation. The control unit 64 may set the resistance value $R_L$ of the resistance element 31R to the geometric mean value $R_A$ of the maximum value $R_{MAX}$ and the minimum value $R_{MIN}$. However, the control unit 64 may not acquire the maximum value $R_{MAX}$ and the minimum value $R_{MIN}$ of the resistance value $R_S$ of the sensor element 31S from a section corresponding to an explanatory variable that is not used in the prediction equation among the plurality of sections. A plurality of explanatory variables may be used in the prediction equation. In this case, the maximum value $R_{MAX}$ and the minimum value $R_{MIN}$ may be acquired in each of a plurality of sections.

Specifically, the control unit 64 acquires, for example, various kinds of information from the outside via the storage unit 61 or the communication unit 62. The various kinds of information include information on a predetermined interval used to divide a voltage waveform into a plurality of sections, and information on a section corresponding to an explanatory variable used in the prediction equation. In the sensor unit 31-1, the information on the section corresponding to the explanatory variable used in the prediction equation is information on the section t1 corresponding to the explanatory variable $X_{11}$. In the sensor unit 31-2, the information on the section corresponding to the explanatory variable used in the prediction equation is information on the section t2 corresponding to the explanatory variable $X_{22}$. In the sensor unit 31-3, the information on the section corresponding to the explanatory variable used in the prediction equation is information on the section t3 corresponding to the explanatory variable $X_{33}$.

The control unit 64 divides the voltage waveform by the predetermined interval along the time axis into a plurality of sections. The control unit 64 acquires the maximum value $R_{MAX}$ and the minimum value $R_{MIN}$ of the resistance value $R_S$ of the sensor element 31S from the section corresponding to the explanatory variable used in the prediction equation among the plurality of sections. In the case of the sensor unit 31-1, the control unit 64 acquires a maximum value $R_{MAX}-1$ and a minimum value $R_{MIN}-1$ of the resistance value $R_S$ of the sensor element 31S of the sensor unit 31-1 from the section t1 of the voltage waveform V1 as illustrated in FIG. 5. In the case of the sensor unit 31-2, the control unit 64 acquires a maximum value $R_{MAX}-2$ and a minimum value $R_{MIN}-2$ of the resistance value $R_S$ of the sensor element 31S of the sensor unit 31-2 from the section t2 of the voltage waveform V2 as illustrated in FIG. 5. In the case of the sensor unit 31-3, the control unit 64 acquires a maximum value $R_{MAX}-3$ and a minimum value $R_{MIN}-3$ of the resistance value $R_S$ of the sensor element 31S of the sensor unit 31-3 from the section t3 of the voltage waveform V3 as illustrated in FIG. 5. However, the control unit 64 may not acquire the maximum value and minimum value of the resistance value $R_S$ of the sensor element 31S from a section corresponding to an explanatory variable that is not used in the prediction equation among the plurality of sections.

The control unit 64 calculates the geometric mean value $R_A$ of the maximum value $R_{MAX}$ and the minimum value $R_{MIN}$. In the case of the sensor unit 31-1, the control unit 64 calculates a geometric mean value $R_A-1$ of the maximum value $R_{MAX}-1$ and the minimum value $R_{MIN}-1$. In the case of the sensor unit 31-2, the control unit 64 calculates a geometric mean value $R_A-2$ of the maximum value $R_{MAX}-2$ and the minimum value $R_{MIN}-2$. In the case of the sensor unit 31-3, the control unit 64 calculates a geometric mean value $R_A-3$ of the maximum value $R_{MAX}-3$ and the minimum value $R_{MIN}-3$.

The control unit 64 outputs a control signal to the resistance element 31R to set the resistance value $R_L$ of the resistance element 31R to the geometric mean value $R_A$. In the case of the sensor unit 31-1, the control unit 64 outputs a control signal to the resistance element 31R of the sensor unit 31-1 to set the resistance value $R_L$ of the resistance element 31R of the sensor unit 31-1 to the geometric mean value $R_A-1$. In the case of the sensor unit 31-2, the control unit 64 outputs a control signal to the resistance element 31R of the sensor unit 31-2 to set the resistance value $R_L$ of the resistance element 31R of the sensor unit 31-2 to the geometric mean value $R_A-2$. In the case of the sensor unit 31-3, the control unit 64 outputs a control signal to the resistance element 31R of the sensor unit 31-3 to set the resistance value $R_L$ of the resistance element 31R of the sensor unit 31-3 to the geometric mean value $R_A-3$.

Here, the control unit 64 may increase the resolution of the entire voltage waveform. In this case, the control unit 64 may acquire the maximum value $R_{MAX}$ and the minimum value $R_{MIN}$ of the resistance value $R_S$ of the sensor element 31S from the entire voltage waveform. Further, the control unit 64 may calculate the geometric mean value $R_A$ of the maximum value $R_{MAX}$ and the minimum value $R_{MIN}$.

[Example Operation of Gas Detection System]

<Operation During Detection of Type and Concentration of Gas>

Figure 8:
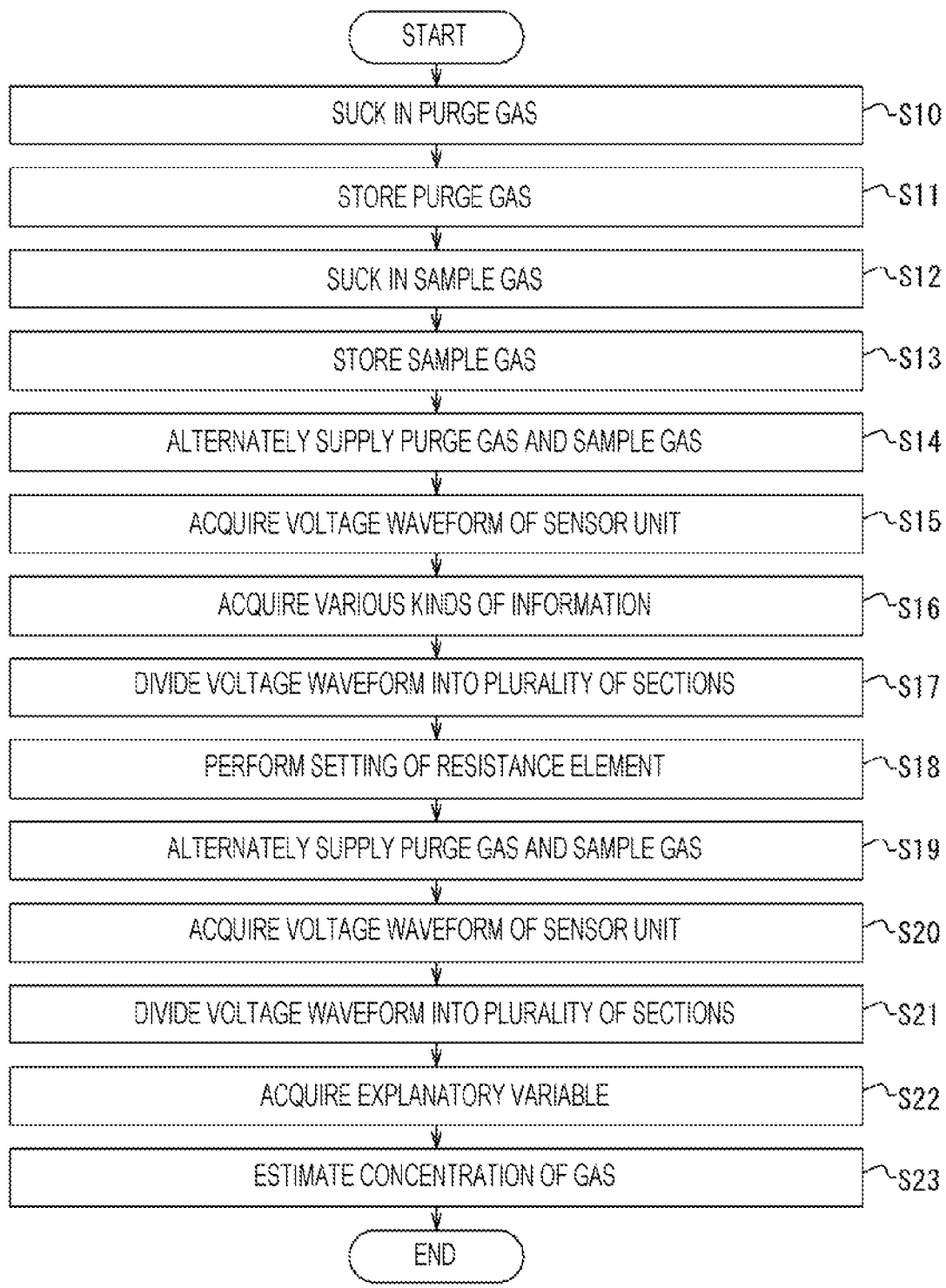
FIG. 8 is a flowchart illustrating the operation of the gas detection system illustrated in FIG. 1 during detection of the type and concentration of a gas.

FIG. 8 is a flowchart illustrating an example operation of the gas detection system 1 illustrated in FIG. 1 during detection of the type and concentration of a gas. The control unit 64 may start a process as illustrated in FIG. 8 after a predetermined time elapses after it is detected that the subject has risen from the toilet seat 2B on the basis of the detection result of the sensor unit 63.

The control unit 64 causes the purge gas to be sucked in through the second suction hole 21 (step S10). The control unit 64 causes the purge gas to be sucked in through the second suction hole 21 to store the purge gas in the second storage tank 41 (step S11).

The control unit 64 causes the sample gas to be sucked in through the first suction hole 20 after a predetermined time elapses after it is detected that the subject has sit on the toilet seat 2B on the basis of the detection result of the sensor unit 63 (step S12). The control unit 64 causes the sample gas to be sucked in through the first suction hole 20 to store the sample gas in the first storage tank 40 (step S13).

The control unit 64 controls the second supply unit 51 and the first supply unit 50 to alternately supply the purge gas and the sample gas to the chamber 30 (step S14). The control unit 64 acquires a voltage waveform output by the sensor unit 31 of the chamber 30 (step S15).

The control unit 64 acquires, for example, various kinds of information from the outside via the storage unit 61 or the communication unit 62 (step S16). The various kinds of information include the information related to the prediction equation described above, and the like.

The control unit 64 divides the voltage waveform output by the sensor unit 31 into a plurality of sections by, for example, dividing the voltage waveform by a predetermined interval along the time axis (step S17).

The control unit 64 performs setting of the resistance element 31R to adjust the resolution of the sensor unit 31 (step S18). The details of the processing of step S18 will be described below with reference to FIG. 12.

The control unit 64 executes the processing of steps S19 and S20 in a way similar to that of the processing of steps S14 and S15.

The control unit 64 executes the processing of step S21 in a way similar to that of the processing of step S17.

The control unit 64 acquires, based on information on computation for acquiring an explanatory variable, which is included in the information related to the prediction equation acquired in the processing of step S16, an explanatory variable used in the prediction equation (step S22).

The control unit 64 substitutes the explanatory variable acquired in the processing of step S22 into the prediction equation to estimate (detect) the concentration of a predetermined gas (step S23). For example, the control unit 64 substitutes the explanatory variables $X_{11}$, $X_{22}$, and $X_{33}$ into prediction equation (1) described above to estimate (detect) the concentration $Y_1$ of the predetermined gas.

The control unit 64 executes the process as illustrated in FIG. 8 for each different prediction equation. The process as illustrated in FIG. 8 is executed for each different prediction equation, thus allowing the type and concentration of a gas to be estimated.

In the processing of step S11, the control unit 64 may determine whether the cleanliness of the purge gas is high. Further, if the cleanliness of the purge gas is high, the control unit 64 may store the purge gas in the second storage tank 41. In this case, the control unit 64 may control the second supply unit 51 to supply the purge gas to the chamber 30. Further, the control unit 64 may determine, based on the detection result of the sensor unit 31, whether the cleanliness of the purge gas is high. When the gas detection system 1 includes a dedicated sensor unit that detects the cleanliness of the purge gas, the control unit 64 may determine whether the cleanliness of the purge gas is high on the basis of the detection result of the dedicated sensor unit.

<Operation for Determining Prediction Equation>

Figure 9:
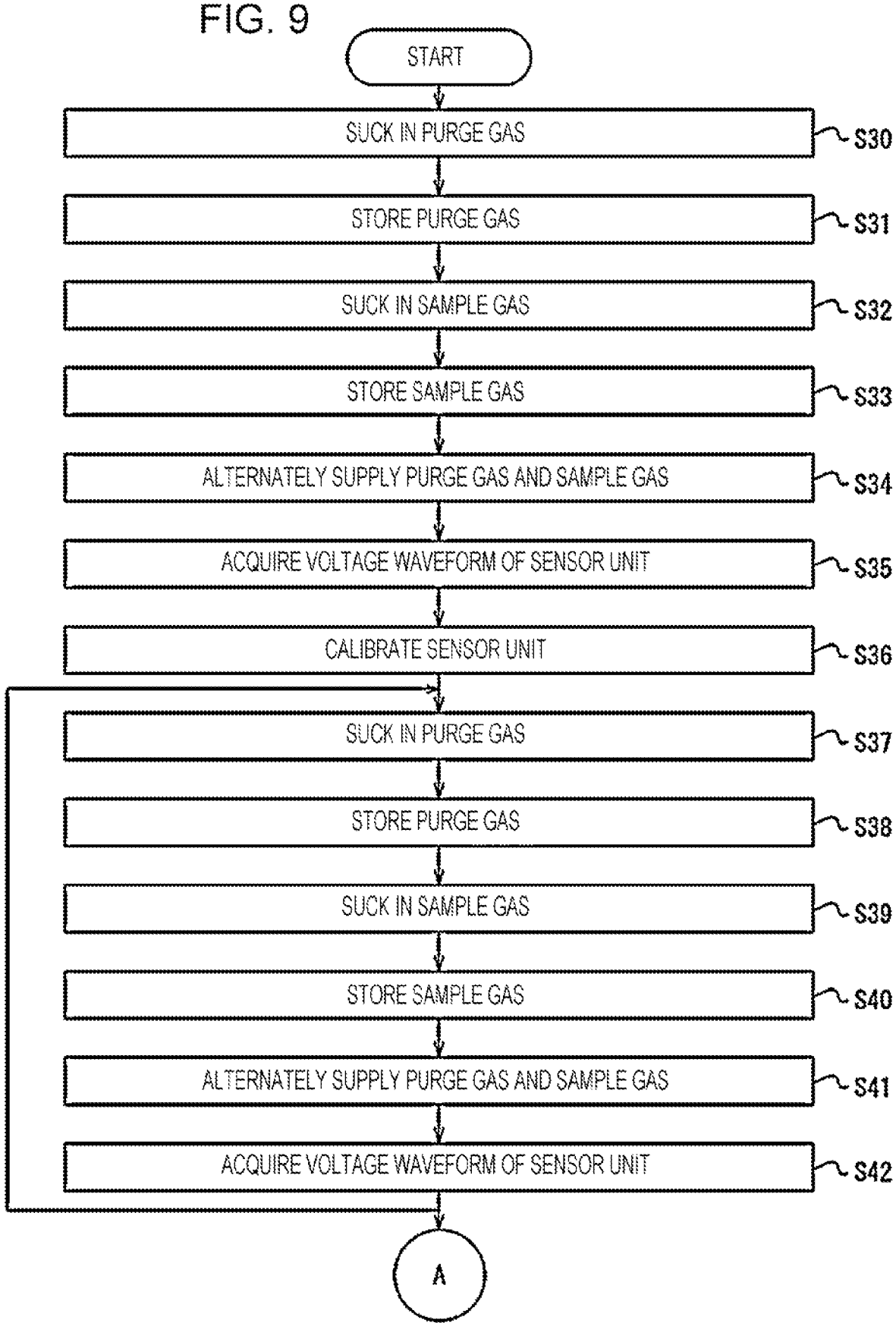
FIG. 9 is a flowchart (part 1) illustrating the operation of the gas detection system illustrated in FIG. 1 when determining a prediction equation.
Figure 10:
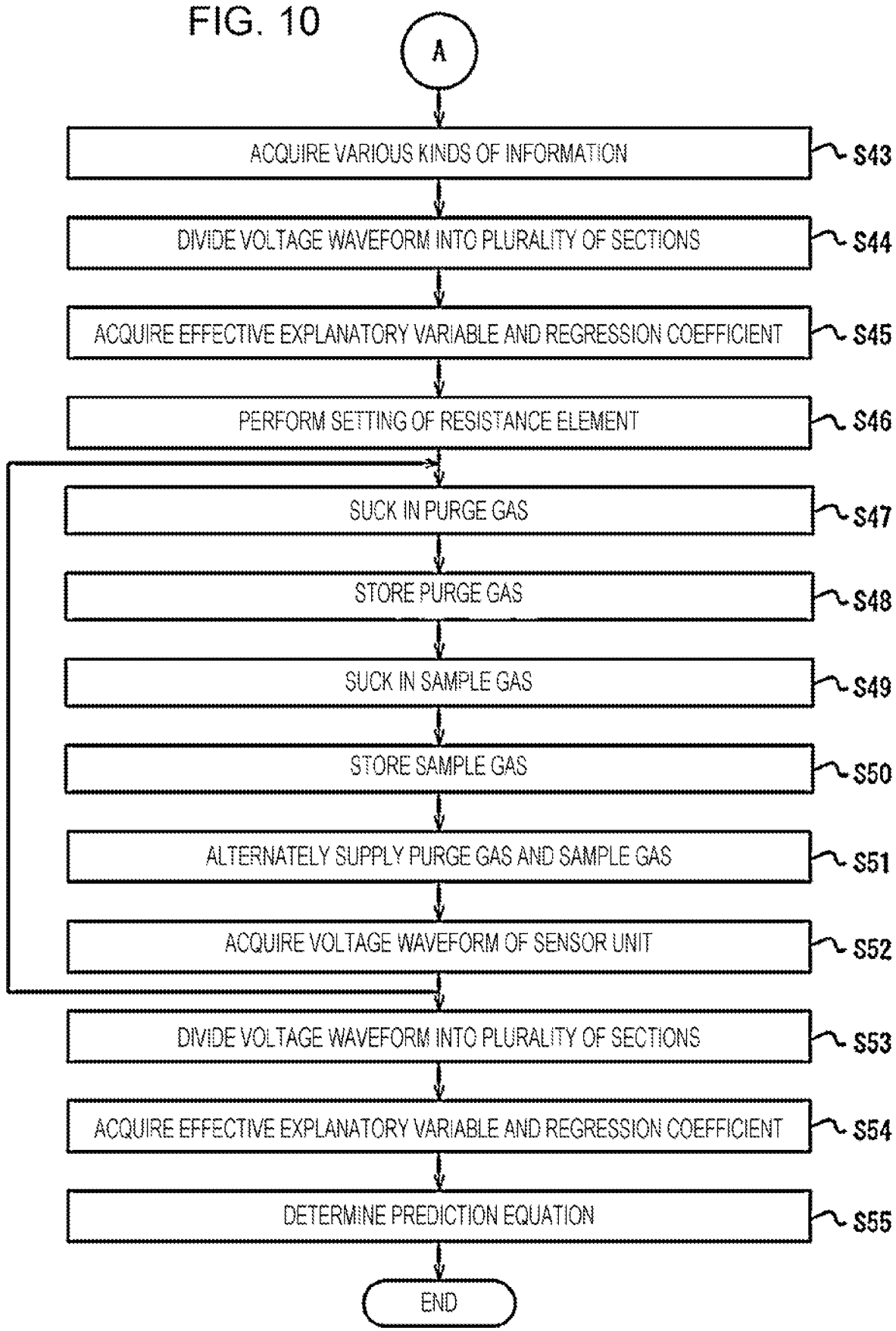
FIG. 10 is a flowchart (part 2) illustrating the operation of the gas detection system illustrated in FIG. 1 when determining a prediction equation.

FIG. 9 and FIG. 10 are a flowchart illustrating the operation of the gas detection system 1 illustrated in FIG. 1 when determining a prediction equation. The process as illustrated in FIG. 9 and FIG. 10 may be executed before the gas detection system 1 is shipped as a product. The control unit 64 may start the process as illustrated in FIG. 9 in accordance with a program incorporated therein in advance or when a control signal for providing an instruction to suck in the purge gas is received from the outside via the communication unit 62. Here, when a prediction equation is to be determined, a plurality of standard gases whose concentrations are maximized may be used as the sample gas.

The control unit 64 executes the processing of steps S30 and 31 in a way similar to that of the processing of steps S10 and S11 as illustrated in FIG. 8.

The control unit 64 executes the processing of steps S32 and 33 in a way similar to that of the processing of steps S12 and 13 as illustrated in FIG. 8 when a control signal for providing an instruction to suck in the sample gas is received from the outside via the communication unit 62.

The control unit 64 executes the processing of steps S34 and S35 in a way similar to that of the processing of steps S14 and S15 as illustrated in FIG. 8. As described above, since a standard gas whose concentration is maximized is used, the amplitude of the voltage waveform of the sensor unit 31 acquired in the processing of step S35 can be maximized.

The control unit 64 calibrates the sensor unit 31 (step S36) on the basis of the voltage waveform of the sensor unit 31 acquired in the processing of step S35. As described above, the amplitude of the voltage waveform of the sensor unit 31 acquired in the processing of step S35 can be maximized. This enables the sensor unit 31 to be more accurately calibrated in the processing of step S36.

The control unit 64 executes the processing of steps S37 to S42 in a way similar to that of the processing of steps S30 to S35. As described above, when a prediction equation is to be determined, a plurality of standard gases are used as the sample gas. Thus, the control unit 64 repeatedly executes the processing of steps S37 to S42 a number of times corresponding to the number of standard gases used.

The control unit 64 proceeds to the process as illustrated in FIG. 10. The control unit 64 acquires various kinds of information from the outside via the storage unit 61 or the communication unit 62 (step S43). The various kinds of information include a model equation in the multiple regression analysis (for example, model equation (2) described above), information related to the standard gases, and the like.

The control unit 64 executes the processing of step S44 in a way similar to that of the processing of step S17 as illustrated in FIG. 8.

For example, the control unit 64 performs supervised machine learning on the voltage waveform to acquire an effective explanatory variable and a regression coefficient in the model equation (for example, model equation (2) described above) (step S45).

The control unit 64 performs setting of the resistance element 31R to adjust the resolution of the sensor unit 31 (step S46). The details of the processing of step S46 will be described below with reference to FIG. 12.

The control unit 64 executes the processing of steps S47 to S52 in a way similar to that of the processing of steps S37 to S42 as illustrated in FIG. 9. The control unit 64 repeatedly executes the processing of steps S47 to S52, in a way similar to that of the processing of steps S37 to S42 as illustrated in FIG. 9, a number of times corresponding to the number of standard gases used to determine the prediction equation. The control unit 64 executes the processing of steps S53 and S54 in a way similar to that of the processing of steps S44 and S45.

The control unit 64 determines a prediction equation for detecting the concentration of the gas n (for example, prediction equation (1) described above) (step S55).

Here, the control unit 64 may not execute the processing of steps S30 to S36 as illustrated in FIG. 9. When the control unit 64 executes the processing of steps S30 to S36 as illustrated in FIG. 9, a plurality of standard gases whose concentrations are maximized may be used only for the processing of steps S30 to S36.

In some cases, the effective explanatory variable and regression coefficient acquired in the processing of step S54 may be different from the effective explanatory variable and regression coefficient acquired in the processing of step S45. In this case, the control unit 64 may execute the processing of steps S30 to S42 as illustrated in FIG. 9 again and then execute the processing of steps S44 and S45 again.

<Operation During Calibration>

Figure 11:
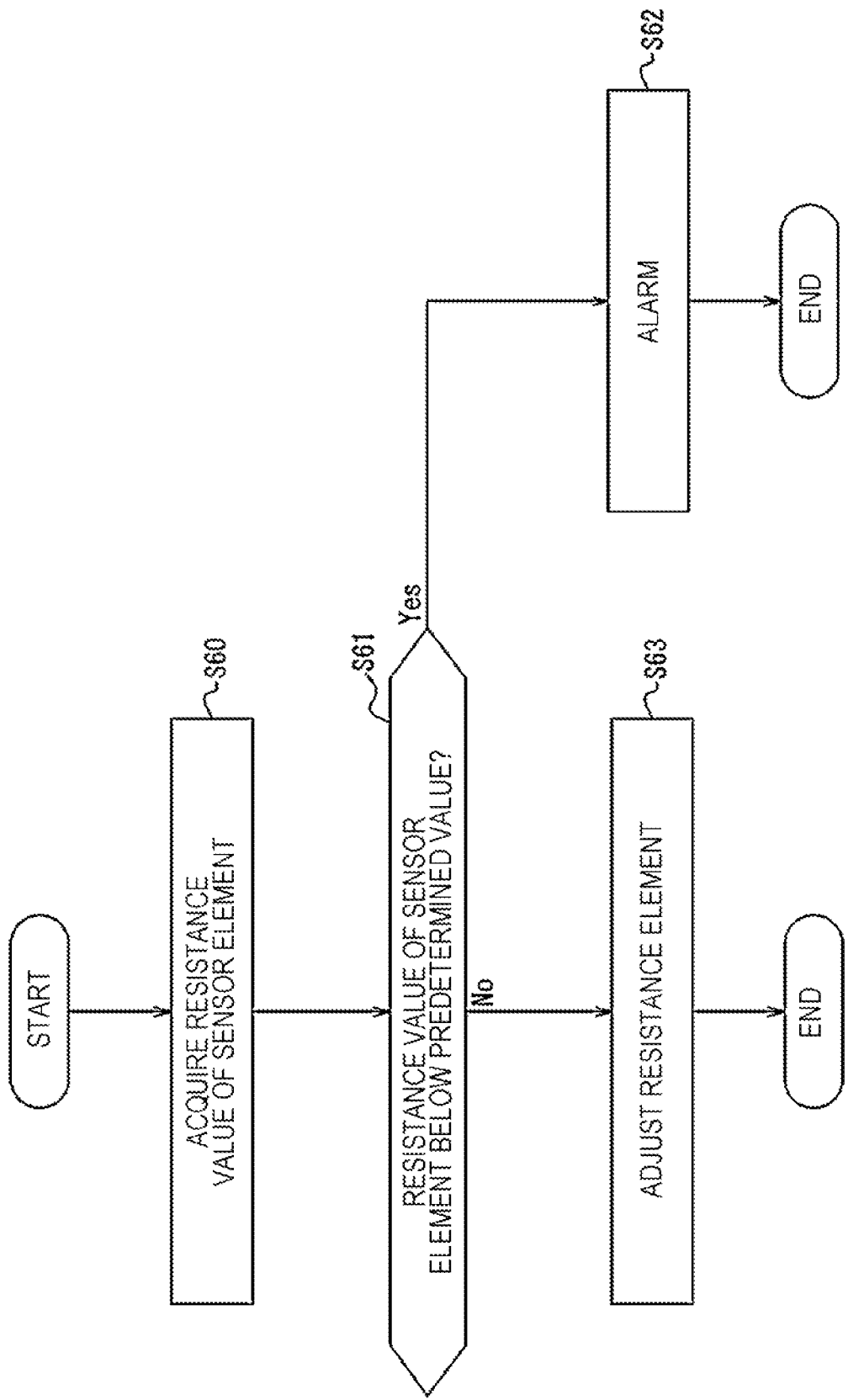
FIG. 11 is a flowchart illustrating the operation of the gas detection system illustrated in FIG. 1 during calibration.

FIG. 11 is a flowchart illustrating an example operation of the gas detection system 1 illustrated in FIG. 1 during calibration. A process as illustrated in FIG. 11 corresponds to the details of the processing of step 36 as illustrated in FIG. 9. However, the control unit 64 may execute the process as illustrated in FIG. 11 independently of the process as illustrated in FIG. 9. After executing the processing of step S35 as illustrated in FIG. 9, the control unit 64 can start the process as illustrated in FIG. 11.

The control unit 64 acquires the resistance value $R_S$ of the sensor element 31S (step S60). The control unit 64 determines whether the resistance value $R_S$ of the sensor element 31S falls below a predetermined value (step S61). If the control unit 64 determines that the resistance value $R_S$ of the sensor element 31S falls below the predetermined value (step S61: Yes), the control unit 64 generates a signal indicating an alarm (step S62). If the control unit 64 determines that the resistance value $R_S$ of the sensor element 31S is greater than or equal to the predetermined value (step S61: No), the control unit 64 proceeds to the processing of step S63.

In the processing of step S63, the control unit 64 adjusts the resistance value $R_L$ of the resistance element 31R in accordance with the resistance value $R_S$ of the sensor element 31S. For example, the control unit 64 may adjust the resistance value $R_L$ of the resistance element 31R in accordance with the resistance value $R_S$ of the sensor element 31S so that the minimum value of the voltage value $V_{RL}$ in the second period T2 becomes near zero or the maximum value of the voltage value $V_{RL}$ in the first period T1 becomes near $V_C$.

Here, in the processing of step S61, the control unit 64 may determine whether the resistance value $R_S$ of the sensor element 31S exceeds the second predetermined value. In this case, if the control unit 64 determines that the resistance value $R_S$ of the sensor element 31S exceeds the second predetermined value, the control unit 64 may generate a signal indicating an alarm.

<Operation During Resolution Adjustment>

Figure 12:
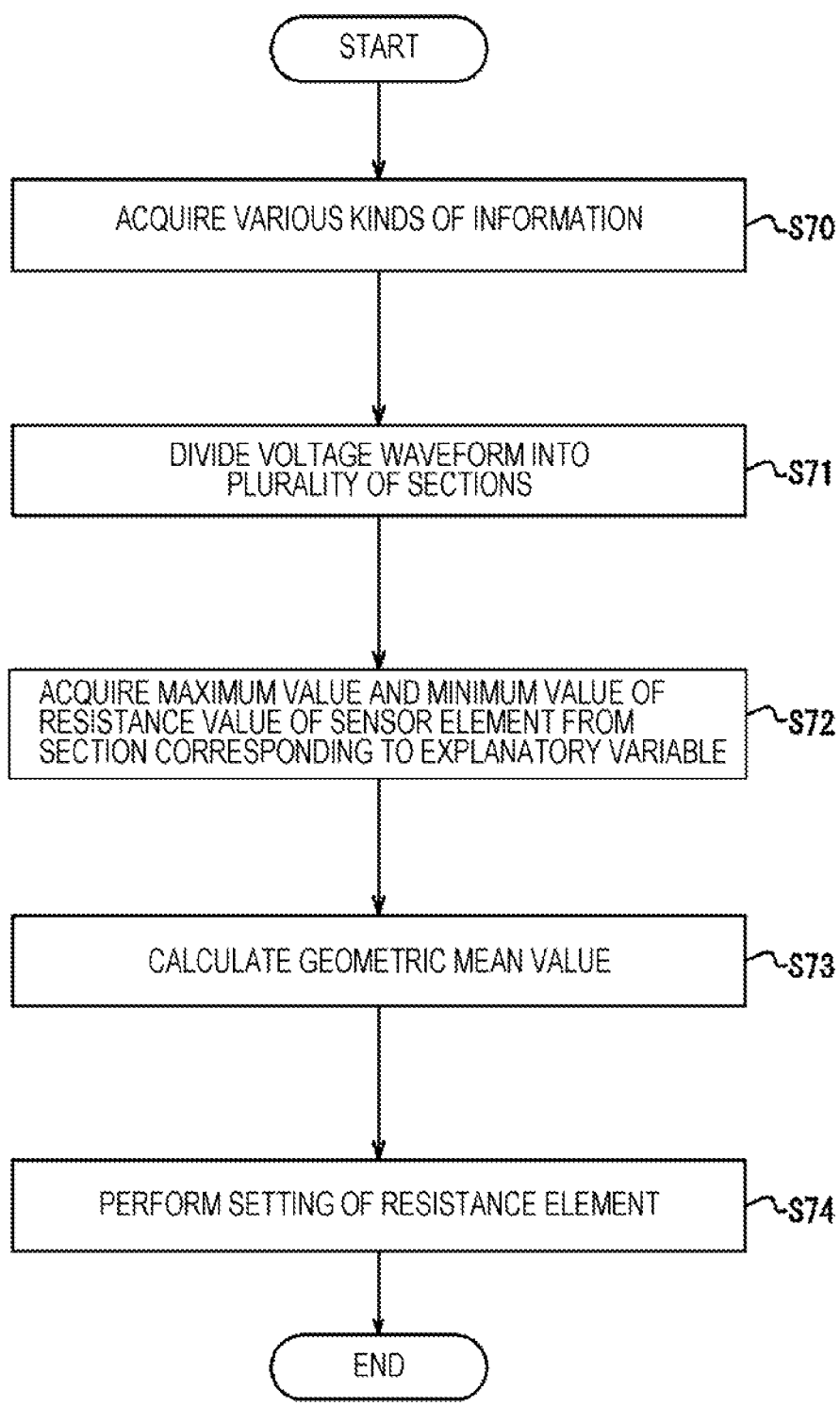
FIG. 12 is a flowchart illustrating the operation of the gas detection system illustrated in FIG. 1 during resolution adjustment.

FIG. 12 is a flowchart illustrating the operation of the gas detection system 1 illustrated in FIG. 1 during resolution adjustment. A process as illustrated in FIG. 12 corresponds to the details of the processing of step S18 as illustrated in FIG. 8 and the details of the processing of step S46 as illustrated in FIG. 10. However, the control unit 64 may execute the process as illustrated in FIG. 12 as a process independent of the processes as illustrated in FIG. 8 and FIG. 10. Here, the control unit 64 can start the process as illustrated in FIG. 12 after executing the processing of step S17 as illustrated in FIG. 8 or after executing the processing of step S45 as illustrated in FIG. 10. In this case, the control unit 64 may execute the process from the processing of step S72 without executing the processing of steps S70 and S71.

The control unit 64 acquires, for example, various kinds of information from the outside via the storage unit 61 or the communication unit 62 (step S70). The various kinds of information include information on a predetermined interval used to divide a voltage waveform into a plurality of sections, and information on a section corresponding to an explanatory variable used in the prediction equation.

The control unit 64 divides the voltage waveform by the predetermined interval along the time axis into a plurality of sections (step S71).

The control unit 64 acquires the maximum value $R_{MAX}$ and the minimum value $R_{MIN}$ of the resistance value $R_S$ of the sensor element 31S from the section corresponding to the explanatory variable used in the prediction equation among the plurality of sections (step S72). In other words, in the processing of step S72, the control unit 64 may not acquire the maximum value $R_{MAX}$ and the minimum value $R_{MIN}$ of the resistance value $R_S$ of the sensor element 31S from a section corresponding to an explanatory variable that is not used in the prediction equation among the plurality of sections. For example, in the case of the sensor unit 31-1, the control unit 64 acquires the maximum value $R_{MAX}$-1 and the minimum value $R_{MIN}$-1 of the resistance value $R_S$ of the sensor element 31S of the sensor unit 31-1 from the section t1 of the voltage waveform V1 as illustrated in FIG. 5.

The control unit 64 calculates the geometric mean value $R_A$ of the maximum value $R_{MAX}$ and the minimum value $R_{MIN}$ (step S73). For example, in the case of the sensor unit 31-1, the control unit 64 calculates the geometric mean value $R_A$-1 of the maximum value $R_{MAX}$-1 and the minimum value $R_{MIN}$-1.

The control unit 64 outputs a control signal to the resistance element 31R to set the resistance value $R_L$ of the resistance element 31R to the geometric mean value $R_A$ (step S74). For example, in the case of the sensor unit 31-1, the control unit 64 outputs a control signal to the resistance element 31R of the sensor unit 31-1 to set the resistance value $R_L$ of the resistance element 31R of the sensor unit 31-1 to the geometric mean value $R_A$-1.

To increase the resolution of the entire voltage waveform, the control unit 64 may not execute the processing of step S70. In this case, in the processing of step S71, the control unit 64 may acquire the maximum value $R_{MAX}$ and the minimum value $R_{MIN}$ of the resistance value $R_S$ of the sensor element 31S from the entire voltage waveform.

As described above, in the gas detection system 1 according to this embodiment, the control unit 64 acquires voltage waveforms of the sensor unit 31 and detects the type and concentration of a gas contained in the sample gas, using a multiple regression analysis using characteristics of the voltage waveforms as explanatory variables. Using a multiple regression analysis, the gas detection system 1 can more accurately estimate the type and concentration of a gas contained in the sample gas. According to this embodiment, therefore, an improved the gas detection system 1 can be provided.

In the gas detection system 1 according to this embodiment, furthermore, the control unit 64 can acquire the maximum value $R_{MAX}$ and the minimum value $R_{MIN}$ of the resistance value $R_S$ of the sensor element 31S of the sensor unit 31. Further, the control unit 64 sets the resistance value $R_L$ of the resistance element 31R of the sensor unit 31 to the geometric mean value of the maximum value $R_{MAX}$ and the minimum value $R_{MIN}$, thereby making it possible to set the resistance value $R_L$ of the resistance element 31R to be equal to the resistance value $R_S$ of the sensor element 31S. Through the process described above, the fluctuation range of the voltage value $V_S$ across the sensor element 31S can be close to a maximum value. Since the fluctuation range of the voltage value $V_S$ becomes close to a maximum value, the ratio of the voltage value $V_S$ to noise increases, and the resolution of the sensor unit 31 can increase.

In the gas detection system 1 according to this embodiment, furthermore, the control unit 64 can acquire the maximum value $R_{MAX}$ and the minimum value $R_{MIN}$ of the resistance value $R_S$ of the sensor element 31S of the sensor unit 31 from, among a plurality of sections, a section corresponding to an explanatory variable used in the prediction equation. Further, the control unit 64 can set the resistance value $R_L$ of the resistance element 31R of the sensor unit 31 to the geometric mean value of the maximum value $R_{MAX}$ and the minimum value $R_{MIN}$. Through the process described above, the resolution of the sensor unit 31 can be increased in accordance with a section corresponding to an explanatory variable used in the prediction equation. Increasing the resolution of the sensor unit 31 in accordance with the section enables accurate acquisition of the explanatory variable used in the prediction equation.

The drawings describing an embodiment according to the present disclosure are schematic. Dimensional ratios and the like in the drawings do not necessarily match the actual ones.

While an embodiment according to the present disclosure has been described with reference to the drawings and examples, it should be noted that various modifications or changes can be easily made by a person skilled in the art on the basis of the present disclosure. Accordingly, it should be noted that these modifications or changes fall within the scope of the present disclosure. For example, the functions and the like included in each component or the like can be rearranged in any manner that is not logically contradictory, and a plurality of components may be combined into one or divided.

For example, in the embodiment described above, the control unit 64 as illustrated in FIG. 3 controls the first supply unit 50 as illustrated in FIG. 2 to cause the sample gas to be sucked in through the first suction hole 20 to store the sample gas in the first storage tank 40. However, the process of the control unit 64 for storing the sample gas in the first storage tank 40 is not limited to this. For example, the control unit 64 may control the third supply unit 52 to cause the sample gas to be sucked in through the first suction hole 20 to store the sample gas in the first storage tank 40. In this case, the control unit 64 causes the valve 20B to connect the first suction hole 20 and the first storage tank 40 to each other and causes the valve 25 to connect the flow path 23-1 and the flow path 27-1 to each other. The control unit 64 further controls the third supply unit 52 to cause the sample gas to be sucked in through the first suction hole 20 to store the sample gas in the first storage tank 40.

For example, in the embodiment described above, the control unit 64 as illustrated in FIG. 3 controls the second supply unit 51 as illustrated in FIG. 2 to cause the purge gas to be sucked in through the second suction hole 21 to store the purge gas in the second storage tank 41. However, the process of the control unit 64 for storing the purge gas in the second storage tank 41 is not limited to this. For example, the control unit 64 may control the third supply unit 52 to cause the purge gas to be sucked in through the second suction hole 21 to store the purge gas in the second storage tank 41. In this case, the control unit 64 causes the valve 21B to connect the second suction hole 21 and the second storage tank 41 to each other and causes the valve 26 to connect the flow path 24-1 and the flow path 27-2 to each other. The control unit 64 further controls the third supply unit 52 to cause the purge gas to be sucked in through the second suction hole 21 to store the purge gas in the second storage tank 41.

Figure 13:
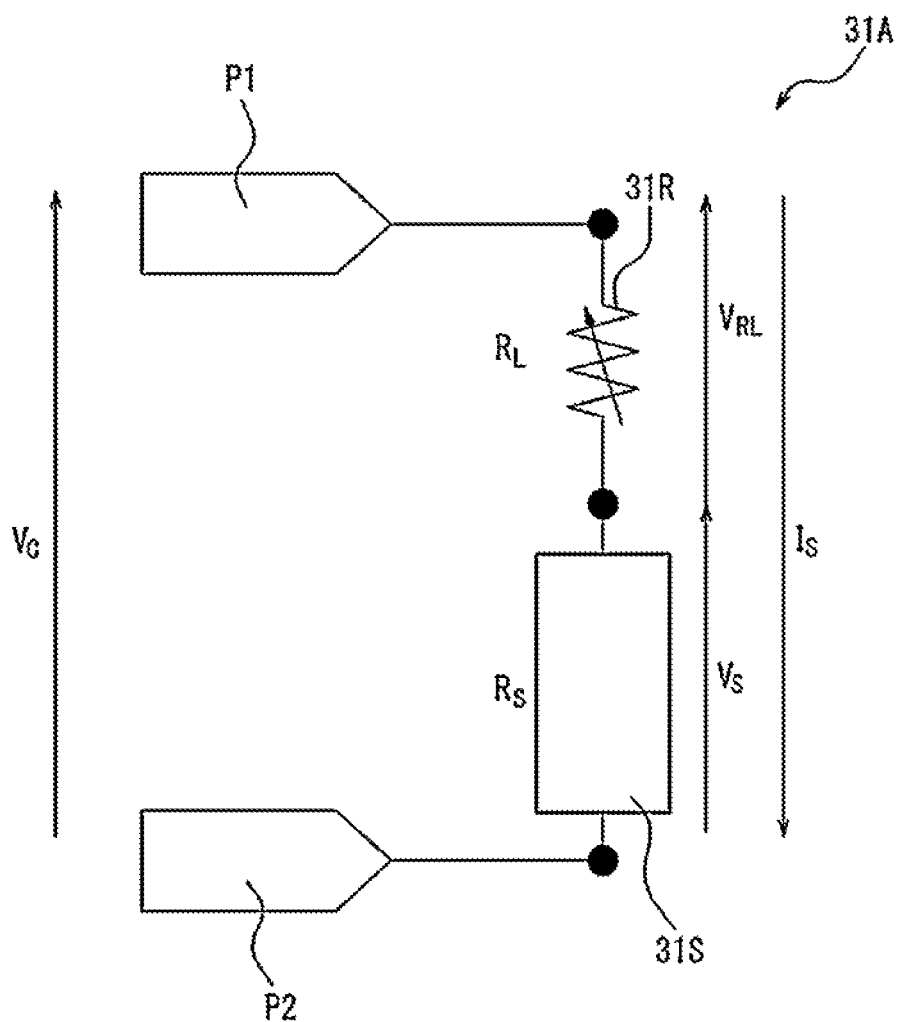
FIG. 13 is a diagram illustrating another example circuit diagram of the sensor unit illustrated in FIG. 2.

For example, in the embodiment described above, in the configuration of the sensor unit 31 as illustrated in FIG. 4, the sensor element 31S is connected to the power supply terminal P1, and the resistance element 31R is connected to the ground terminal P2. However, the configuration of the sensor unit according to the present disclosure is not limited to the configuration as illustrated in FIG. 4. The configuration of the sensor unit according to the present disclosure may be, for example, a configuration as illustrated in FIG. 13. A sensor unit 31A as illustrated in FIG. 13 includes a sensor element 31S and a resistance element 31R connected in series. In FIG. 13, one end of the sensor element 31S is connected to the ground terminal P2. In FIG. 13, the other end of the sensor element 31S is connected to one end of the resistance element 31R. In FIG. 13, the other end of the resistance element 31R is connected to the power supply terminal P1.

For example, in the embodiment described above, the control unit 64 controls the first supply unit 50 and the second supply unit 51 to alternately supply the purge gas and the sample gas to the chamber 30. However, the control unit 64 may control a single supply unit to alternately supply the purge gas and the sample gas to the chamber 30. In this case, the gas detection system 1 may adopt configurations as illustrated in FIG. 14, FIG. 15, and FIG. 16.

Figure 14:
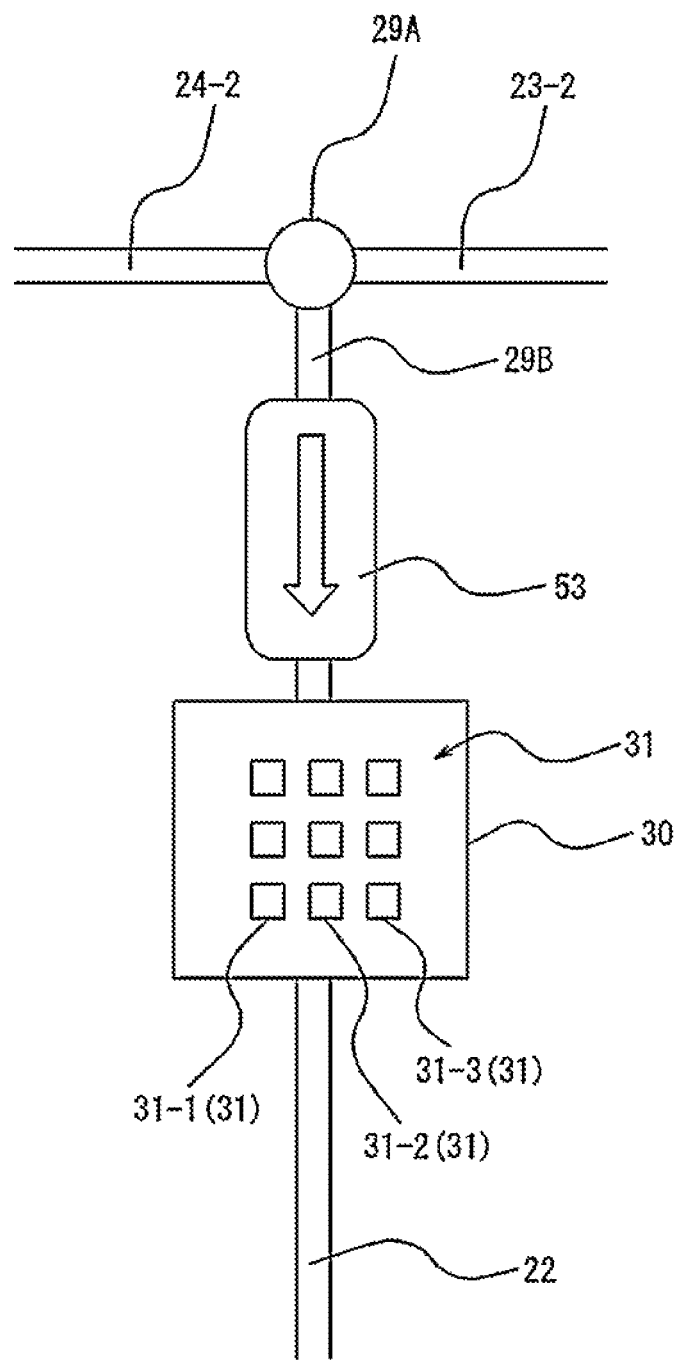
FIG. 14 is a diagram illustrating other example 1 of the configuration illustrated in FIG. 2.

In the configuration as illustrated in FIG. 14, a valve 29A, a flow path 29B, and a fourth supply unit 53 are used. The valve 29A is located between the flow path 23-2, the flow path 24-2, and the flow path 29B. The valve 29A includes a connection port connected to the flow path 23-2, a connection port connected to the flow path 24-2, and a connection port connected to the flow path 29B. The valve 29A may be constituted by a valve such as an electromagnetically driven valve, a piezoelectrically driven valve, or a motor-driven valve. The valve 29A switches the connection state between the flow path 23-2, the flow path 24-2, and the flow path 29B under the control of the control unit 64. For example, the valve 29A switches the connection state between them to a state in which the flow path 23-2 and the flow path 29B are connected to each other, a state in which the flow path 24-2 and the flow path 29B are connected to each other, or a state in which the flow path 23-2, the flow path 24-2, and the flow path 29B are not connected to each other. One end of the flow path 29B is connected to the valve 29A. The other end of the flow path 29B is connected to the chamber 30. The flow path 29B may be constituted by a tubular member such as a resin tube or a metal or glass pipe. The fourth supply unit 53 is attached to the flow path 29B. The arrow illustrated in the fourth supply unit 53 indicates the direction in which the fourth supply unit 53 sends a gas. The fourth supply unit 53 may be constituted by a piezoelectric pump, a motor pump, or the like. The fourth supply unit 53 is capable of supplying the sample gas and the purge gas to the sensor unit 31. Specifically, when the valve 29A connects the flow path 23-2 and the flow path 29B to each other, the fourth supply unit 53 is capable of supplying the sample gas stored in the first storage tank 40 as illustrated in FIG. 2 to the chamber 30. When the valve 29A connects the flow path 24-2 and the flow path 29B to each other, the fourth supply unit 53 is capable of supplying the purge gas stored in the second storage tank 41 illustrated in FIG. 2 to the chamber 30.

In the configuration as illustrated in FIG. 14, the control unit 64 as illustrated in FIG. 3 causes the valve 29A to connect the flow path 23-2 and the flow path 29B to each other and controls the fourth supply unit 53 to supply the sample gas stored in the first storage tank 40 as illustrated in FIG. 2 to the chamber 30. Further, the control unit 64 causes the valve 29A to connect the flow path 24-2 and the flow path 29B to each other and controls the fourth supply unit 53 to supply the purge gas stored in the second storage tank 41 as illustrated in FIG. 2 to the chamber 30.

Figure 15:
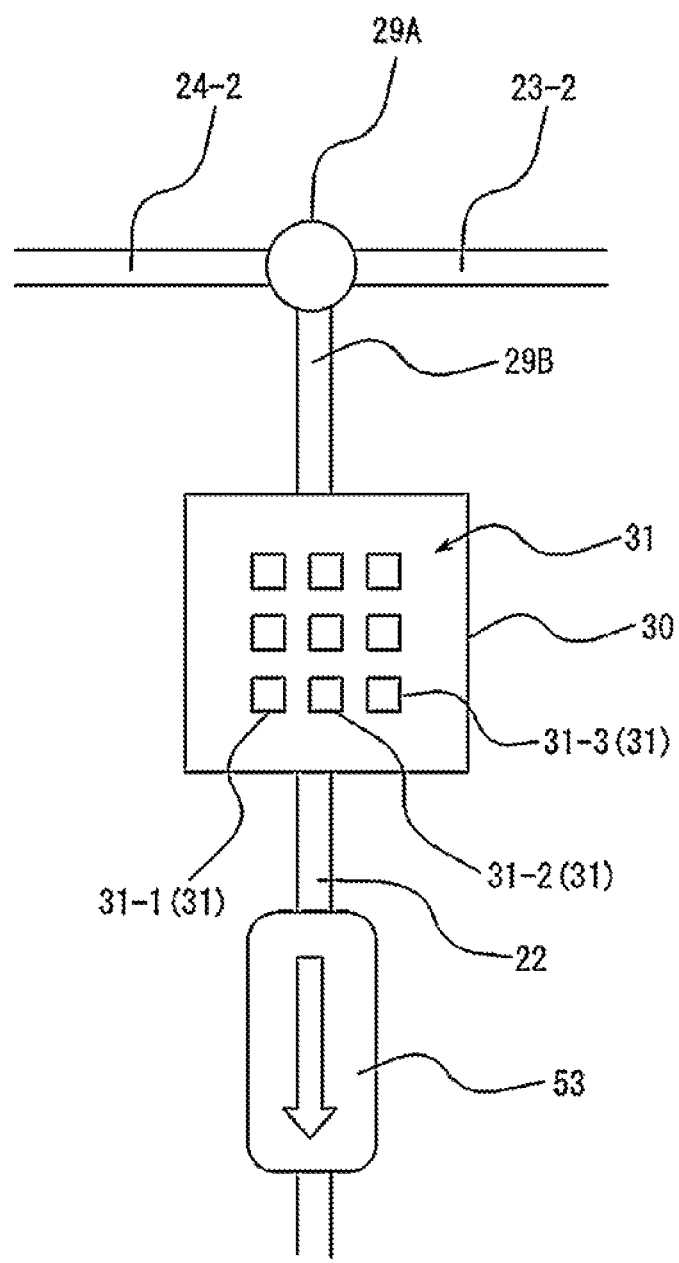
FIG. 15 is a diagram illustrating other example 2 of the configuration illustrated in FIG. 2.
Figure 16:
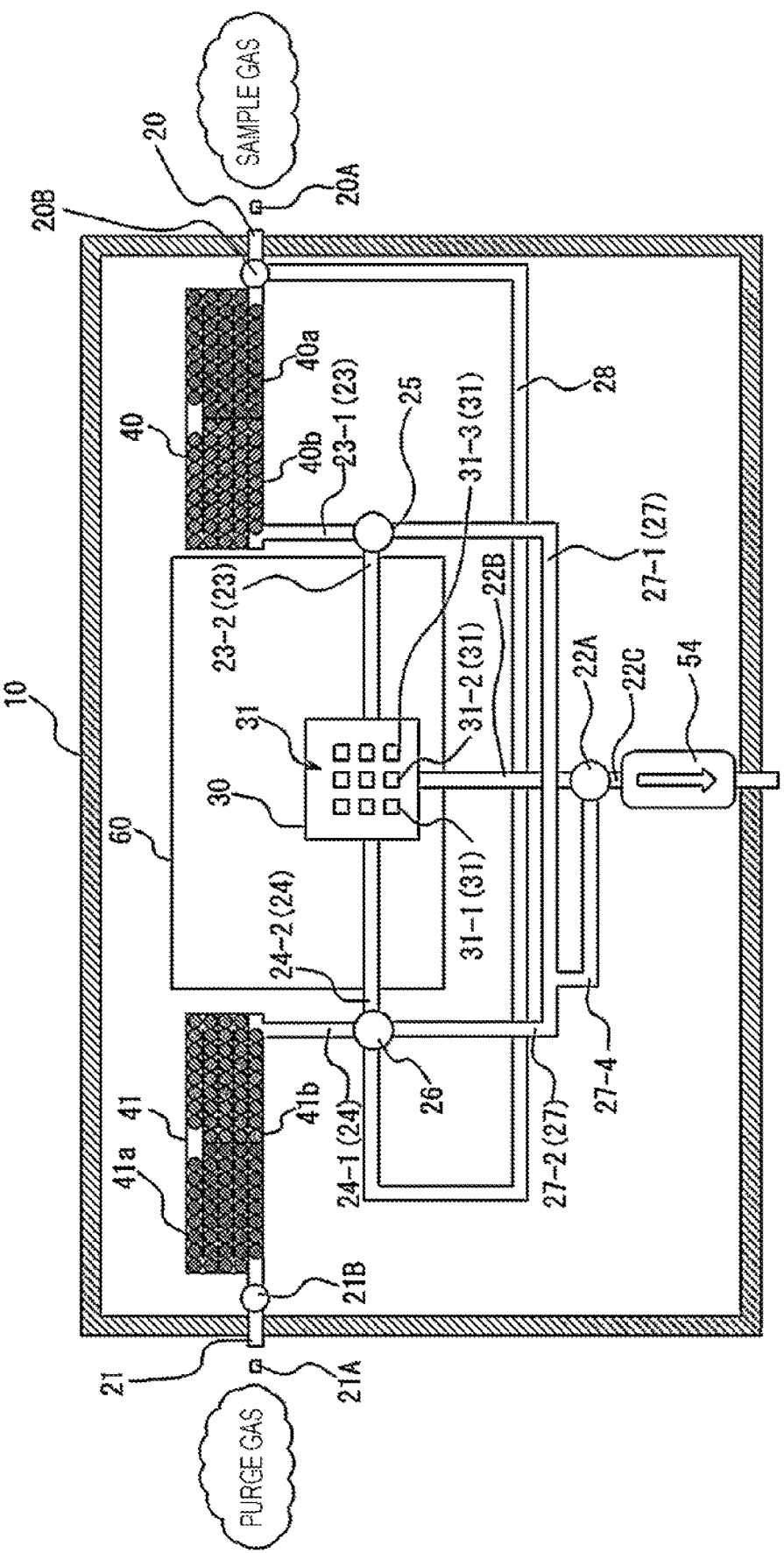
FIG. 16 is a diagram illustrating other example 3 of the configuration illustrated in FIG. 2.

In the configuration as illustrated in FIG. 15, as in the configuration as illustrated in FIG. 14, a valve 29A, a flow path 29B, and a fourth supply unit 53 are used. In the configuration as illustrated in FIG. 15, however, the fourth supply unit 53 is attached to the discharge path 22. In the configuration as illustrated in FIG. 15, when the valve 29A connects the flow path 23-2 and the flow path 29B to each other, the fourth supply unit 53 is capable of supplying the sample gas stored in the first storage tank 40 as illustrated in FIG. 2 to the chamber 30. When the valve 29A connects the flow path 24-2 and the flow path 29B to each other, the fourth supply unit 53 is capable of supplying the purge gas stored in the second storage tank 41 as illustrated in FIG. 2 to the chamber 30.

In the configuration as illustrated in FIG. 15, the control unit 64 as illustrated in FIG. 3 causes the valve 29A to connect the flow path 23-2 and the flow path 29B to each other and controls the fourth supply unit 53 to supply the sample gas stored in the first storage tank 40 as illustrated in FIG. 2 to the chamber 30. Further, the control unit 64 causes the valve 29A to connect the flow path 24-2 and the flow path 29B to each other and controls the fourth supply unit 53 to supply the purge gas stored in the second storage tank 41 as illustrated in FIG. 2 to the chamber 30.

A gas detection system 1A as illustrated in FIG. 16 includes a valve 22A, a flow path 22B, a discharge path 22C, the flow path 27-4, and a fifth supply unit 54. The valve 22A includes a connection port connected to the flow path 22B, a connection port connected to the discharge path 22C, and a connection port connected to the flow path 27-4. The valve 22A may be constituted by a valve such as an electromagnetically driven valve, a piezoelectrically driven valve, or a motor-driven valve. The valve 22A switches the connection state between the flow path 22B, the discharge path 22C, and the flow path 27-4 under the control of the control unit 64 as illustrated in FIG. 3. For example, the valve 22A switches the connection state between them to a state in which the flow path 27-4 and the discharge path 22C are connected to each other or a state in which the flow path 22B and the discharge path 22C are connected to each other. Alternatively, the valve 22A switches the connection state to a state in which the flow path 22B, the discharge path 22C, and the flow path 27-4 are not connected to each other. One end of the flow path 22B is connected to the chamber 30. The other end of the flow path 22B is connected to the valve 22A. One end of the discharge path 22C is connected to the valve 22A. The other end of the discharge path 22C may be exposed to the outside of the toilet bowl 2A, like the discharge path 22 as illustrated in FIG. 1. One end of the flow path 27-4 is connected to the other end of the flow path 27-1 and the other end of the flow path 27-2. The other end of the flow path 27-4 is connected to the valve 22A. The flow path 22B, the discharge path 22C, and the flow path 27-4 may be each constituted by a tubular member such as a resin tube or a metal or glass pipe. The fifth supply unit 54 is attached to the discharge path 22C. The arrow illustrated in the fifth supply unit 54 indicates the direction in which the fifth supply unit 54 sends a gas. The fifth supply unit 54 may be constituted by a piezoelectric pump, a motor pump, or the like. The fifth supply unit 54 is capable of supplying the sample gas from the first suction hole 20 to the first storage tank 40. The fifth supply unit 54 is capable of supplying the purge gas from the second suction hole 21 to the second storage tank 41. The fifth supply unit 54 is capable of supplying the sample gas and the purge gas to the sensor unit 31.

In the configuration as illustrated in FIG. 16, the control unit 64 as illustrated in FIG. 3 causes the valve 20B to connect the first suction hole 20 and the first storage tank 40 to each other and causes the valve 25 to connect the flow path 23-1 and the flow path 27-1 to each other. Further, the control unit 64 as illustrated in FIG. 3 causes the valve 22A to connect the flow path 27-4 and the discharge path 22C to each other. In addition, the control unit 64 as illustrated in FIG. 3 controls the fifth supply unit 54 to cause the sample gas to be sucked in through the first suction hole 20 to store the sample gas in the first storage tank 40.

In the configuration as illustrated in FIG. 16, the control unit 64 as illustrated in FIG. 3 causes the valve 21B to connect the second suction hole 21 and the second storage tank 41 to each other and causes the valve 26 to connect the flow path 24-1 and the flow path 27-2 to each other. Further, the control unit 64 as illustrated in FIG. 3 causes the valve 22A to connect the flow path 27-4 and the discharge path 22C to each other. In addition, the control unit 64 as illustrated in FIG. 3 controls the fifth supply unit 54 to cause the purge gas to be sucked in through the second suction hole 21 to store the purge gas in the second storage tank 41.

In the configuration as illustrated in FIG. 16, the control unit 64 as illustrated in FIG. 3 causes the valve 25 to connect the flow path 23-1 and the flow path 23-2 to each other and causes the valve 22A to connect the flow path 22B and the discharge path 22C to each other. Further, the control unit 64 as illustrated in FIG. 3 controls the fifth supply unit 54 to supply the sample gas stored in the first storage tank 40 to the chamber 30. Further, the control unit 64 as illustrated in FIG. 3 causes the valve 26 to connect the flow path 24-1 and the flow path 24-2 to each other and causes the valve 22A to connect the flow path 27-4 and the discharge path 22C to each other. Further, the control unit 64 as illustrated in FIG. 3 controls the fifth supply unit 54 to supply the purge gas stored in the second storage tank 41 to the chamber 30.

For example, in the embodiment described above, as illustrated in FIG. 3, the gas detection system 1 has been described as a single device. However, the gas detection system according to the present disclosure is not limited to the single device and may include a plurality of independent devices. The gas detection system according to the present disclosure may have, for example, a configuration as illustrated in FIG. 17.

Figure 17:
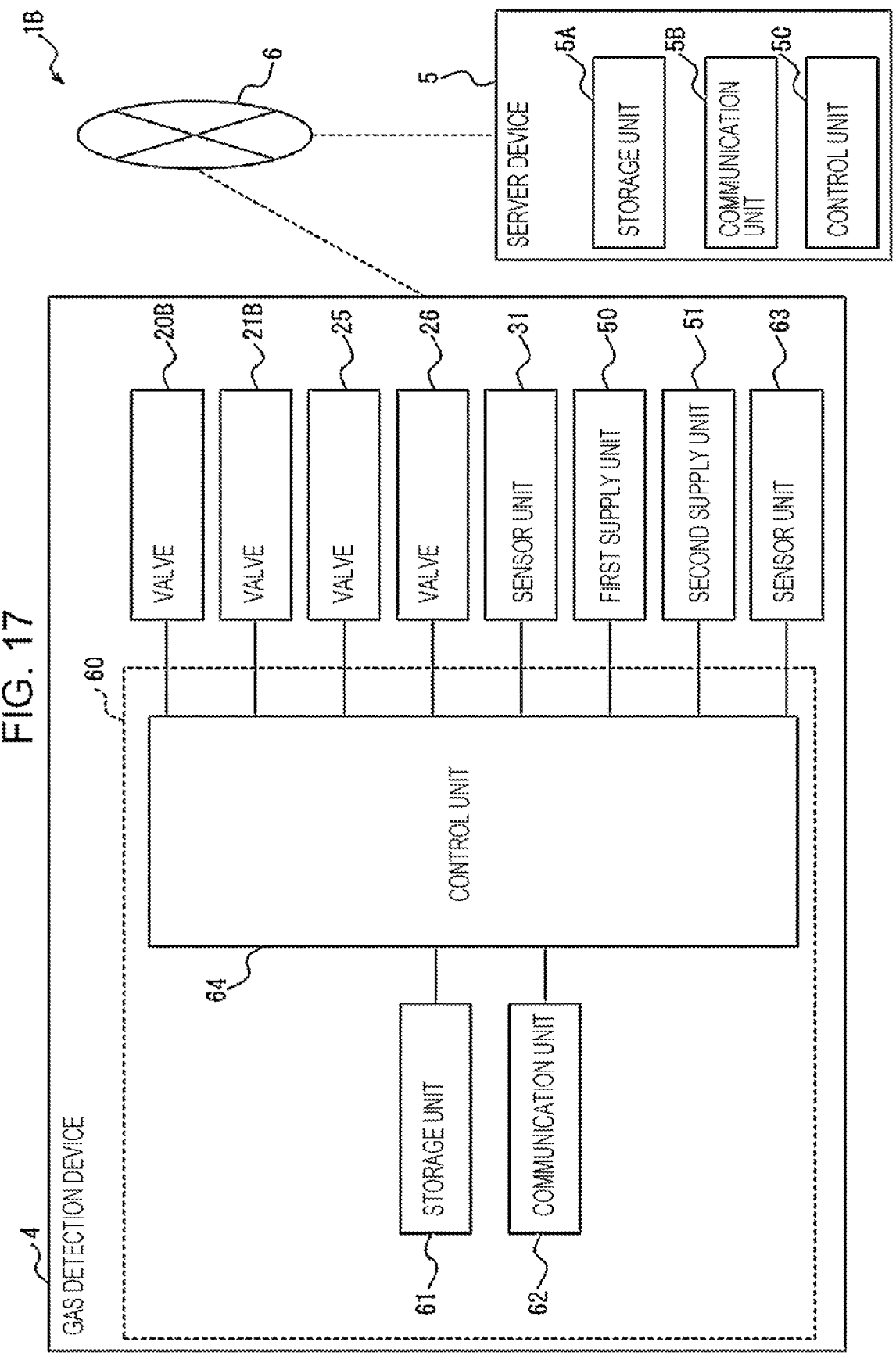
FIG. 17 is a functional block diagram of a gas detection system according to another embodiment of the present disclosure.

A gas detection system 1B as illustrated in FIG. 17 includes a gas detection device 4 and a server device 5. The gas detection device 4 and the server device 5 are capable of communicating with each other via a network 6. A portion of the network 6 may be wired or wireless. The gas detection device 4 has a configuration similar to the configuration of the gas detection system 1 as illustrated in FIG. 2 and FIG. 3. The server device 5 includes a storage unit 5A, a communication unit 5B, and a control unit 5C. The control unit 5C is capable of executing the processes of the control unit 64 as illustrated in FIG. 3 described above. For example, the control unit 5C can acquire a voltage waveform output by the sensor unit 31 as illustrated in FIG. 2 via the communication unit 5B and the network 6. Further, the control unit 5C can detect the type and concentration of a gas contained in the sample gas, using a multiple regression analysis using characteristics of the voltage waveform as explanatory variables.

For example, a portion of the first suction hole 20, that is, a sample gas suction portion, may be installed on the inside of the toilet bowl 2A or at the boundary between the inside and outside of the toilet bowl 2A. Further, a portion of the second suction hole 21, that is, a purge gas suction portion, may be installed on the outside of the toilet bowl 2A.

For example, the control unit 64 may alternately switch the purge gas and the sample gas and acquire a plurality of voltage waveforms from the sensor unit 31.

For example, the control unit 64 may supply to the chamber 30 a sample gas for which a section corresponding to an explanatory variable is not set. The period during which the sample gas is supplied to the chamber 30 is hereinafter referred to also as "supply period". In this case, the supply period in which a section corresponding to an explanatory variable is not set may be earlier than the supply period in which a section corresponding to an explanatory variable is set. Here, in the earliest supply period, the sensor unit 31 may be exposed to the purge gas for a long time until immediately before the earliest supply period. Accordingly, the voltage waveform of the sample gas in the earliest supply period and the voltage waveform of the sample gas in the subsequent supply period may be different. In this case, explanatory variables may vary greatly. Supplying to the chamber 30 a sample gas for which a section corresponding to an explanatory variable is not set can reduce such a variation in explanatory variable.

For example, in a period from voltage measurement of a gas by the sensor unit 31 to the subsequent suction period, the purge gas may be introduced into the first storage tank 40, the second storage tank 42, or the sensor unit 31. This period may include a period during which at least any one of the first storage tank 40 and the second storage tank 41 is heated. This configuration allows the first storage tank 40 and the adsorbent 40*a* to be refreshed, and the second storage tank 41 and the adsorbents 41*a* and 41*b* to be refreshed.

In the present disclosure, descriptions such as "first" and "second" are identifiers for distinguishing the respective configurations. The configurations distinguished by the descriptions such as "first" and "second" in the present disclosure may be interchangeably numbered. For example, a first suction hole and a second suction hole may exchange their identifiers "first" and "second". The identifiers are exchanged simultaneously. Even after the identifiers are exchanged, the respective configurations are distinguishable. The identifiers may be deleted. Configurations without identifiers are distinguished using reference numerals. Only the description of identifiers such as "first" and "second" in the present disclosure should not be used as a basis for interpreting the order of the configurations or for determining the presence of identifiers with smaller numbers.

REFERENCE SIGNS LIST 1, 1A, 1B gas detection system
2 toilet
2A toilet bowl
2B toilet seat
3 electronic device
3A display unit
4 gas detection device
5 server device
5A storage unit
5B communication unit
5C control unit
10 housing
20 first suction hole
21 second suction hole
20A, 21A air blower
20B, 21B valve
22, 22C discharge path
22B, 23, 23-1, 23-2, 24, 24-1, 24-2, 27, 27-1, 27-2, 27-3, 27-4, 28, 29B flow path
22A, 25, 26, 29A valve
30 chamber
31, 31-1, 31-2, 31-3, 31A sensor unit
31S sensor element
31R resistance element
40 first storage tank
41 second storage tank
40*a*, 40*b*, 41*a*, 41*b* adsorbent
50 first supply unit
51 second supply unit
52 third supply unit
53 fourth supply unit
54 fifth supply unit
60 circuit board
61 storage unit
62 communication unit
63 sensor unit
64 control unit
P1 power supply terminal
P2 ground terminal

The invention claimed is:

1. A gas detection system comprising:
a sensor unit that outputs a signal corresponding to a concentration of a specific gas;
a supply unit that supplies a sample gas and a purge gas to the sensor unit;
a first suction hole through which the sample gas is sucked in;
a first storage tank connected to the first suction hole, the first storage tank for storing the sample gas sucked from the first suction hole;
a valve that is located between the first suction hole and the first storage tank and switches a connection state between the first suction hole and the first storage tank; and
a control unit that controls the supply unit to alternately supply the sample gas and the purge gas to the sensor unit, wherein
the control unit acquires an output by the sensor unit, and detects a type and concentration of a gas contained in the sample gas based on the output by the sensor
wherein the supply unit supplies the sample gas stored in the first storage tank to the sensor unit,
wherein the control unit controls the valve to switch the connection state between the first suction hole and the first storage tank.

2. The gas detection system according to claim 1, wherein the type and concentration of the gas contained in the sample gas are detected using a prediction equation determined by the multiple regression analysis and an explanatory variable among the explanatory variables used in the prediction equation.

3. The gas detection system according to claim 2, wherein the sensor unit includes a resistance element and a sensor element that are connected in series, and
the control unit sets a resistance value of the resistance element to be equal to a resistance value of the sensor element.

4. The gas detection system according to claim 3, wherein the control unit
acquires a maximum value and a minimum value of the resistance value of the sensor element from the voltage waveform output by the sensor unit, and
sets the resistance value of the resistance element to a geometric mean value of the maximum value and the minimum value to be equal to the resistance value of the sensor element.

5. The gas detection system according to claim 4, wherein the control unit divides the voltage waveform of the sensor unit into a plurality of sections along a time axis, acquires the maximum value and the minimum value from a section of the plurality of sections corresponding to the explanatory variable used in the prediction equation, and sets the resistance value of the resistance element to a geometric mean value of the maximum value and the minimum value acquired from the section corresponding to the explanatory variable used in the prediction equation.

6. The gas detection system according to claim 5, wherein the control unit does not acquire the maximum value and the minimum value from another section of the plurality of sections corresponding to an explanatory variable that is not used in the prediction equation.

7. The gas detection system according to claim 3, wherein the control unit
acquires the resistance value of the sensor element before detecting the type and concentration of the gas contained in the sample gas, and generates a signal indicating an alarm when the acquired resistance value of the sensor element falls below a predetermined value.

8. The gas detection system according to claim 7, wherein the control unit adjusts the resistance value of the resistance element in accordance with the resistance value of the sensor element when the acquired resistance value of the sensor element is greater than or equal to the predetermined value.

9. The gas detection system according to claim 1, further comprising;
a first suction hole through which the sample gas is sucked in;
a second suction hole through which the purge gas is sucked in;
a first storage tank connected to the first suction hole, the first storage tank for storing the sample gas; and
a second storage tank connected to the second suction hole, the second storage tank for storing the purge gas, wherein
the supply unit supplies the sample gas stored in the first storage tank to the sensor unit, and the supply unit supplies the purge gas stored in the second storage tank to the sensor unit.

10. The gas detection system according to claim 1, further comprising;
a second suction hole through which the purge gas is sucked in;
the supply unit supplies the purge gas sucked from the second suction hole to the sensor.

11. The gas detection system according to claim 1, wherein the gas detection system further comprises: a first flow path that connects the first suction hole and the first storage tank; and a second flow path that connects the first storage tank and the sensor unit, wherein the valve is located in the first flow path.

12. The gas detection system according to claim 1, wherein the gas detection system further comprises a second suction hole that sucks the purge gas and is different from the first suction hole.

* * * * *